(12) United States Patent
Ryono et al.

(10) Patent No.: US 7,557,143 B2
(45) Date of Patent: Jul. 7, 2009

(54) THYROID RECEPTOR LIGANDS

(75) Inventors: Denis E. Ryono, Princeton, NJ (US);
Jon J. Hangeland, Morrisville, PA (US);
Todd J. Friends, Bordentown, NJ (US);
Tamara Dejneka, Skillman, NJ (US);
Pratik Devasthale, Plainsboro, NJ (US);
Yolanda V. Caringal, Lawrenceville, NJ (US);
Minsheng Zhang, Warren, NJ (US);
Arthur M. P. Doweyko, Long Valley, NJ (US);
Johan Malm, Trangsund (SE);
Andrei Sanin, Varby (SE)

(73) Assignee: Bristol-Myers Squibb Company, Princeton, NJ (US)

( * ) Notice: Subject to any disclaimer, the term of this patent is extended or adjusted under 35 U.S.C. 154(b) by 653 days.

(21) Appl. No.: 10/826,100

(22) Filed: Apr. 15, 2004

(65) Prior Publication Data

US 2005/0004184 A1 Jan. 6, 2005

Related U.S. Application Data

(60) Provisional application No. 60/463,774, filed on Apr. 18, 2003.

(51) Int. Cl.
 A61K 31/165 (2006.01)
 A61K 31/19 (2006.01)
 C07C 239/00 (2006.01)
 C07C 325/00 (2006.01)
 C07C 229/00 (2006.01)
 C07C 59/00 (2006.01)

(52) U.S. Cl. .................. 514/568; 514/617; 562/426; 562/433; 562/452; 562/465; 564/161

(58) Field of Classification Search .................. 514/522, 514/617, 615, 568; 558/410; 564/155, 163, 564/161; 562/426, 433, 452, 465
See application file for complete search history.

(56) References Cited

U.S. PATENT DOCUMENTS 3,239,345 A 3/1966 Hodge et al.

(Continued)

FOREIGN PATENT DOCUMENTS

EP 0 221 025 5/1987

(Continued)

OTHER PUBLICATIONS

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

(Continued)

*Primary Examiner*—Taylor Victor Oh
(74) *Attorney, Agent, or Firm*—Maureen S. Gibbons; Elliott Korsen

(57) ABSTRACT

Thyroid receptor ligands are provided which have the general formula I

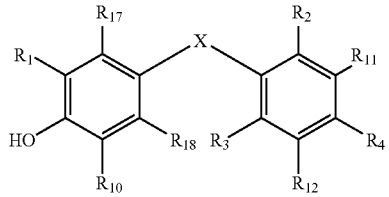

wherein:
R1 is

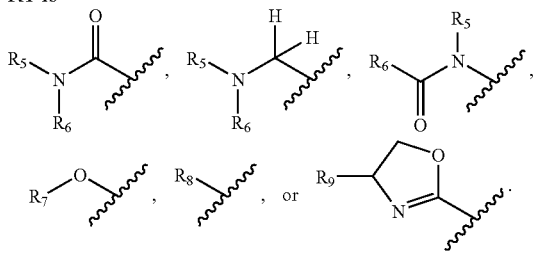

R2 and R3 are the same or different and are hydrogen, halogen, alkyl of 1 to 4 carbons or cycloalkyl of 3 to 5 carbons, provided that at least one of R2 and R3 is other than hydrogen;
R4 is

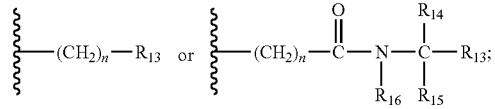

R5 and R6 are the same or different and are selected from hydrogen, aryl, heteroaryl, alkyl, cycloalkyl, aralkyl or heteroaralkyl.
R7 is aryl, heteroaryl, alkyl, aralkyl, or heteroaralkyl;
R8 is aryl, heteroaryl, or cycloalkyl;
R9 is R7 or hydrogen;
R10 is hydrogen, halogen, cyano or alkyl;
R11 and R12 are each independently selected from the group consisting of hydrogen, halogen, alkoxy, hydroxy (—OH) cyano, and alkyl;
R13 is carboxylic acid (COOH) or esters thereof, phosphonic and phosphinic acid or esters thereof, sulfonic acid, tetrazole, hydroxamic acid, thiazolidinedione, acylsulfonamide, or other carboxylic acid surrogates known in the art;
R14 and R15 may be the same or different and are selected from hydrogen and alkyl, or R14 and R15 may be joined together forming a chain of 2 to 5 methylene groups [—(CH2)m-, m=2, 3, 4 or 5], thus forming 3- to 6-membered cycloalkyl rings;
R16 is hydrogen or alkyl of 1 to 4 carbons;
R17 and R18 are the same or different and selected from hydrogen, halogen and alkyl;
n is 0 or an integer from 1 to 4;
X is oxygen (—O—), sulfur (—S—), sulfonyl (—SO$_2$—), sulfenyl (—SO—) selenium (—Se—), carbonyl (—CO—), amino (—NH—) or methylene (—CH2-); wherein the substituents are as described herein.
In addition, a method is provided for preventing, inhibiting or treating diseases or disorders associated with metabolism dysfunction or which are dependent upon the expression of a T$_3$ regulated gene, wherein a compound as described above is administered in a therapeutically effective amount.

9 Claims, No Drawings

U.S. PATENT DOCUMENTS

| | | | |
|---|---|---|---|
| 3,983,140 | A | 9/1976 | Endo et al. |
| 4,027,009 | A | 5/1977 | Grier et al. |
| 4,036,979 | A | 7/1977 | Asato |
| 4,231,938 | A | 11/1980 | Monaghan et al. |
| 4,346,227 | A | 8/1982 | Terahara et al. |
| 4,389,416 | A * | 6/1983 | Plattner ..................... 514/539 |
| 4,411,890 | A | 10/1983 | Momany |
| 4,448,784 | A | 5/1984 | Glamkowski et al. |
| 4,450,171 | A | 5/1984 | Hoffman et al. |
| 4,499,289 | A | 2/1985 | Baran et al. |
| 4,613,610 | A | 9/1986 | Wareing |
| 4,647,576 | A | 3/1987 | Hoefle et al. |
| 4,681,893 | A | 7/1987 | Roth |
| 4,686,237 | A | 8/1987 | Anderson |
| 4,759,923 | A | 7/1988 | Buntin et al. |
| 4,871,721 | A | 10/1989 | Biller |
| 4,924,024 | A | 5/1990 | Biller |
| 5,006,530 | A | 4/1991 | Angerbauer et al. |
| 5,177,080 | A | 1/1993 | Angerbauer et al. |
| 5,273,995 | A | 12/1993 | Roth |
| 5,354,772 | A | 10/1994 | Kathawala |
| 5,385,929 | A | 1/1995 | Bjorge et al. |
| 5,401,772 | A | 3/1995 | Yokoyama et al. |
| 5,488,064 | A | 1/1996 | Sher |
| 5,491,134 | A | 2/1996 | Sher et al. |
| 5,541,204 | A | 7/1996 | Sher et al. |
| 5,595,872 | A | 1/1997 | Wetterau, II et al. |
| 5,612,359 | A | 3/1997 | Murugesan |
| 5,686,104 | A | 11/1997 | Mills et al. |
| 5,712,279 | A | 1/1998 | Biller et al. |
| 5,712,396 | A | 1/1998 | Magnin et al. |
| 5,739,135 | A | 4/1998 | Biller et al. |
| 5,760,246 | A | 6/1998 | Biller et al. |
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,885,983 | A | 3/1999 | Biller et al. |
| 5,962,440 | A | 10/1999 | Sulsky |
| 6,043,265 | A | 3/2000 | Murugesan et al. |
| 6,090,854 | A | 7/2000 | Epperson |
| 6,184,231 | B1 | 2/2001 | Hewawasam et al. |

FOREIGN PATENT DOCUMENTS

| | | |
|---|---|---|
| EP | 0 142 146 | 8/1988 |
| FR | 2 596 393 | 10/1987 |
| GB | 1463219 | 2/1977 |
| WO | WO 86/03488 | 6/1986 |
| WO | WO 86/07054 | 12/1986 |
| WO | WO 89/07110 | 8/1989 |
| WO | WO 89/07111 | 8/1989 |
| WO | WO 93/04081 | 3/1993 |
| WO | WO 97/21993 | 6/1997 |
| WO | WO 99/00353 | 1/1999 |
| WO | WO 00/01389 | 1/2000 |

OTHER PUBLICATIONS

Biller, S.A. et al., "Squalene Synthase Inhibitors", Current Pharmaceutical Design, vol. 2, No. 1, pp. 1-40 (1996).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51 (Jun. 1987).

Chan, D.M.T. et al., "New N- and O-Arylations with Phenylboronic Acids and Cupric Acetate", Tetrahedron Letters, vol. 39, pp. 2933-2936 (1998).

Chiellini, G. et al., "A high-affinity subtype-selective agonist ligand for the thyroid hormone receptor", Chemistry & Biology, vol. 5, No. 6, pp. 299-306 (1998).

Corey, E.J. et al., "Application of Unreactive Analogs of Terpenoid Pyrophosphates to Studies of Multistep Biosynthesis: Demonstration That 'Presqualene Pyrophosphate' Is an Essential Intermediate on the Path to Squalene", J. Am. Chem. Soc., vol. 98, No. 5, pp. 1291-1293 (1976).

Couladouros, E.A. et al., "A general synthetic route towards bastadins. Part 1: Synthesis of the eastern part of bastadins 4-16", Tetrahedron Letters, vol. 40, pp. 7023-7026 (1999).

Dibbo, A. et al., "The Synthesis of Thyroxine and Related Compounds. Part XVII. The Preparation of Some Additional Compounds related to Thyroxine", J. Chem. Soc., pp. 2890-2902 (1961).

Edwards, J.P. et al., "Nonsteroidal Androgen Receptor Agonists Based on 4-(trifluoromethyl)-2H- pyrano[3,2-g]quinotin-2-one", Bioorganic & Medicinal Chemistry Letters, vol. 9, pp. 1003-1008 (1999).

Evans, D.A. et al., "Synthesis of Diaryl Ethers through the Copper-Promoted Arylation of Phenols with Arylboronic Acids. An Expedient Synthesis of Thyroxine", Tetrahedron Letters, vol. 39, pp. 2937-2940 (1998).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Greene, T.W. et al., Protective Groups in Organic Synthesis, Third Edition, John Wiley & Sons, Inc., publ., pp. xi-xii (table of contents) (1999).

Guo, Z.-W. et al., "Enzymatic Oxidative Phenolic Coupling", J. Org. Chem., vol. 62, No. 20, pp. 6700-6701 (1997).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, No. 2, pp. 210-212 (1999).

Hara, S., "Ileal $Na^+$/bile acid cotransporter inhibitors", Drugs of the Future, vol. 24, No. 4, pp. 425-430 (1999).

Harrington, C.R., "Synthesis of a Sulphur-containing Analogue of Thyroxine", Biochem. J., vol. 43, pp. 434-437 (1948).

Hickey, D.M.B. et al., "Synthesis of Thyroid Hormone Analogues. Part 2. Oxidative Coupling Approach to SK&F L-94901", J. Chem. Soc. Perkin Trans. I, pp. 3097-3102 (1988).

Hickey, D.M.B. et al., "Synthesis of Thyroid Hormone Analogues. Part 3. Iodonium Salt Approaches to SK&F L-94901", J. Chem. Soc. Perkin Trans. I, pp. 3103-3111 (1988).

Homer, L. et al., "Die Synthese brücken-analoger Thyroninverbindungen", Chemische Berichte, vol. 85, pp. 520-530 (1952).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Kalinin, A.V. et al., "The Directed Ortho Metalation-Ullmann Connection. A New Cu(I)-Catalyzed Variant for the Synthesis of Substituted Diaryl Ethers", J. Org. Chem. vol. 64, No. 9, pp. 2986-2987 (1999).

Krause, B.R. et al., Chapter 6: "ACAT Inhibitors: Physiologic Mechanisms for Hypolipidemic and Anti-Atherosclerotic Activities in Experimental Animals", Inflammation: Mediators Pathways, CRC Press Inc., publ., Ruffolo, Jr., R.R. et al., eds., pp. 173-198 (1995).

Marcoux, J.-F. et al., "A General Copper-Catalyzed Synthesis of Diaryl Ethers", vol. 119, No. 43, pp. 10539-10540 (1997).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salamonczyk, G.M. et al., "A Concise Synthesis of Thyroxine ($T_4$) and 3,5,3'-Triiodo-L-thyronine ($T_3$)", Tetrahedron Letters, vol. 38, No. 40, pp. 6965-6968 (1997).

Salisbury, B.G. et al., "Hypocholesterolemic activity of a novel inhibitor of cholesterol absorption, SCH 48461", Atherosclerosis, vol. 115, pp. 45-63 (1995).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of Future, vol. 24, No. 1, pp. 9-15 (1999).

Stanton, J.L. et al., "Synthesis and Biological Activity of Phenoxyphenyl Oxamic Acid Derivatives Related to L-Thyronine", Bioorganic & Medicinal Chemistry Letters, vol. 10, pp. 1661-1663 (2000).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Wermuth, C.G. et al., Chapter 31: "Designing Prodrugs and Bioprecursors I: Carrier Prodrugs", The Practice of Medicinal Chemistry, Academic Press, publ., Wermuth, C.G., ed., pp. 671-696 (1996).

Yokoyama, N. et al., "Synthesis and Structure-Activity Relationships of Oxamic Acid and Acetic Acid Derivatives Related to L-Thyronine", J. Med. Chem., vol. 38, No. 4, pp. 695-707 (1995).

* cited by examiner

THYROID RECEPTOR LIGANDS

RELATED APPLICATIONS

This application claims priority benefit under Title 35 § 119(e) of U.S. Provisional Application No. 60/463,774, filed Apr. 18, 2003, the contents of which are herein incorporated by reference.

FIELD OF THE INVENTION

This invention relates to novel compounds which are thyroid receptor ligands, and to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, metabolic rate, body temperature and mood, and influence blood levels of serum low density lipoprotein (LDL). Thus, in hypothyroidism there is weight gain, high levels of LDL cholesterol, and depression. In hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals, may be restricted by certain detrimental effects from thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Furthermore, useful thyroid agonist drugs should minimize the potential for undesired consequences due to locally induced hypothyroidism, i.e. sub-normal levels of thyroid hormone activity in certain tissues or organs. This can arise because increased circulating thyroid hormone agonist concentrations may cause the pituitary to suppress the secretion of thyroid stimulating hormone (TSH), thereby reducing thyroid hormone synthesis by the thyroid gland (negative feedback control). Since endogenous thyroid hormone levels are reduced, localized hypothyroidism can result wherever the administered thyroid agonist drug fails to compensate for the reduction in endogenous hormone levels in specific tissues. For example, if the thyroid agonist drug does not penetrate the blood-brain barrier, the effects of TSH suppression can lead to CNS hypothyroidism and associated risks such as depression.

Development of specific and selective thyroid hormone receptor ligands, particularly agonists of the thyroid hormone receptor could lead to specific therapies for these common disorders, while avoiding the cardiovascular and other toxicity of native thyroid hormones. Tissue-selective thyroid hormone agonists may be obtained by selective tissue uptake or extrusion, topical or local delivery, targeting to cells through other ligands attached to the agonist and targeting receptor subtypes. Tissue selectivity can also be achieved by selective regulation of thyroid hormone responsive genes in a tissue specific manner.

Accordingly, the discovery of compounds that are thyroid hormone receptor ligands, particularly selective agonists of the thyroid hormone receptor, may demonstrate a utility for the treatment or prevention of diseases or disorders associated with thyroid hormone activity, for example: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and (6) osteoporosis in combination with a bone resorption inhibitor.

SUMMARY OF THE INVENTION

In accordance with the illustrative embodiments and demonstrating features of the present invention, compounds are provided which are thyroid receptor ligands, and have the general formula I

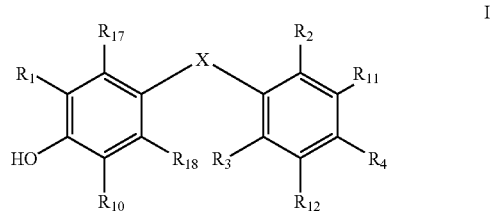

wherein:

R1 is

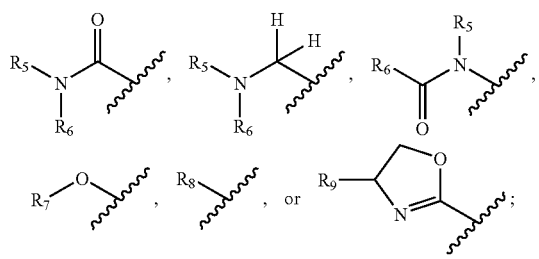

R2 and R3 are the same or different and are hydrogen, halogen, alkyl of 1 to 4 carbons or cycloalkyl of 3 to 5 carbons, provided that at least one of R2 and R3 is other than hydrogen;

R4 is

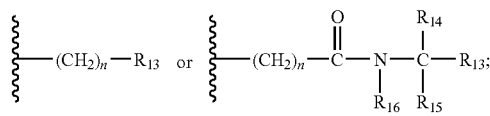

R5 and R6 are the same or different and are selected from hydrogen, aryl, heteroaryl, alkyl, cycloalkyl, aralkyl or heteroaralkyl.

R7 is aryl, heteroaryl, alkyl, aralkyl, or heteroaralkyl;

R8 is aryl, heteroaryl, or cycloalkyl;

R9 is R7 or hydrogen;

R10 is hydrogen, halogen, cyano or alkyl;

R11 and R12 are each independently selected from the group consisting of hydrogen, halogen, alkoxy, hydroxy, cyano, and alkyl;

R13 is carboxylic acid (COOH) or esters thereof, phosphonic and phosphinic acid or esters thereof, sulfonic acid, tetrazole, hydroxamic acid, thiazolidinedione, acylsulfonamide, or other carboxylic acid surrogates known in the art;

R14 and R15 may be the same or different and are selected from hydrogen and alkyl, or R14 and R15 may be joined together forming a chain of 2 to 5 methylene groups [—(CH2)m-, m=2, 3, 4 or 5], thus forming 3- to 6-membered cycloalkyl rings;

R16 is hydrogen or alkyl of 1 to 4 carbons;

R17 and R18 are the same or different and selected from hydrogen, halogen and alkyl;

n is 0 or an integer from 1 to 4; and

X is oxygen (—O—), sulfur (—S—), sulfonyl (—SO$_2$—), sulfenyl, (—SO—) selenium (—Se—), carbonyl (—CO—), amino (—NH—) or methylene (—CH2-).

The definition of formula I above includes all prodrugesters, stereoisomers and pharmaceutically acceptable salts of formula I.

The compounds of formula I are thyroid hormone receptor ligands and include compounds which are, for example, selective agonists, partial agonists, antagonists or partial antagonists of the thyroid receptor. Preferably, the compounds of formula I possess activity as agonists of the thyroid receptor, preferably selective agonists of the thyroid receptor-beta, and may be used in the treatment of diseases or disorders associated with thyroid receptor activity. In particular, the compounds of formula I may be used in the treatment of diseases or disorders associated with metabolism dysfunction or which are dependent upon the expression of a T$_3$ regulated gene, such as obesity, hypercholesterolemia, atherosclerosis, cardiac arrhythmias, depression, osteoporosis, hypothyroidism, goiter, thyroid cancer, glaucoma, skin disorders or diseases and congestive heart failure.

The present invention is directed to the compounds of formula I, pharmaceutical compositions employing such compounds and methods of using such compounds. In particular, the present invention includes a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the thyroid receptor, particularly, the thyroid receptor-beta, such as the diseases or disorders defined above and hereinafter, wherein a therapeutically effective amount of a compound of formula I is administered to a mammalian, i.e., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another compound of the invention and/or another type of therapeutic agent, is administered to a mammalian patient in need of treatment.

Preferably compounds of this invention include embodiments of formula I wherein

R1 is

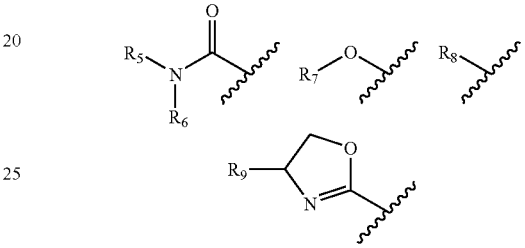

R2 and R3 are the same or different and are selected from bromine, chlorine or methyl;

R4 is

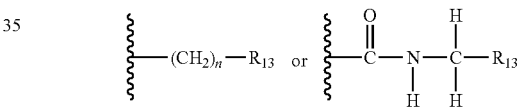

and n is 1 or 2;

One of R5 and R6 is hydrogen and the other is alkyl or aralkyl;

R7 is aryl, heteroaryl, alkyl, aralkyl, or heteroaralkyl;

R8 is aryl, heteroaryl, or cycloalkyl;

R9 is methyl, phenyl or isopropyl;

R10 is hydrogen or methyl;

One of R11 and R12 is hydrogen and the other is either hydrogen or methyl;

R13 is carboxyl;

R14, R15, R16, R17 and R18 are hydrogen;

X is oxygen (—O—), sulfur (—S—) or methylene (—CH2-).

DETAILED DESCRIPTION OF THE INVENTION

The following abbreviations have the indicated meanings:
Ph=phenyl
Bn=benzyl
t-Bu=tertiary butyl
Me=methyl
Et=ethyl
THF=tetrahydrofuran
Et$_2$O=diethyl ether
EtOAc=ethyl acetate
DMF=dimethyl formamide
MeOH=methanol EtOH=ethanol
i-PrOH=isopropanol
HOAc or AcOH=acetic acid
TFA=trifluoroacetic acid
i-Pr$_2$NEt=diisopropylethylamine
Et$_3$N=triethylamine
DMAP=4-dimethylaminopyridine
NaBH$_4$=sodium borohydride
KOH=potassium hydroxide
NaOH=sodium hydroxide
LiOH=lithium hydroxide
K$_2$CO$_3$=potassium carbonate
NaHCO$_3$=sodium bicarbonate
Ph$_3$P=triphenylphosphine
Ar=argon
N$_2$=nitrogen
min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
NMR=nuclear magnetic resonance
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
TLC=thin layer chromatography
HPLC=high performance liquid chromatography
LC/MS=high performance liquid chromatography/mass spectrometry
MS or Mass Spec=mass spectrometry The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "alkyl" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl. As defined and claimed herein, the term "alkyl" includes alkyl groups as defined above optionally substituted with 1 to 4 substituents which may halo, for example F, Br, Cl or I or CF$_3$, alkoxy, aryl, aryloxy, aryl(aryl) or diaryl, arylalkyloxy, alkenyl, alkynyl, cycloalkyl, cycloalkenyl, cycloalkylalkyloxy, optionally substituted amino, hydroxy, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, alkylthio or carboxyl (or alkyl ester thereof).

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 8 carbons, preferably 3 to 6 carbons, forming the ring. As defined and claimed herein, the term "cycloalkyl" includes cycloalkyl groups as defined above optionally substituted with 1 or more substituents, such as those defined for alkyl.

The term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl). As defined and claimed herein, the term "aryl" includes aryl groups as defined above optionally substituted through any available carbon atom(s) with 1 or more substituents, such as halo, alkyl, haloalkyl, alkoxy, haloalkoxy, alkenyl, trifluoromethyl, trifluoromethoxy, alkynyl, hydroxy, amino, nitro, cyano, carboxyl(or alkyl ester thereof) or any of the other substituents described for alkyl.

Unless otherwise indicated, the term "heteroaryl" or "heteroaromatic" as used herein alone or as part of another group refers to a 5- or 6-membered aromatic ring which includes 1, 2, 3 or 4 hetero atoms such as nitrogen, oxygen, or sulfur, and such rings fused to an aryl, cycloalkyl, heteroaryl or cycloheteroalkyl ring (e.g. benzothiophenyl, indole), and includes possible N-oxides. As defined and claimed herein, the term "heteroaryl" includes heteroaryl groups as defined above optionally substituted through any available carbon atom(s) with 1 or more substituents, such as any of the substituents described for alkyl or aryl.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. As defined and claimed herein, the term "alkenyl" includes alkenyl groups as defined above optionally substituted through any available carbon atom(s) with 1 or more substituents, such as any of the substituents described for alkyl or aryl.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. As defined and claimed herein, the term "alkynyl" includes alkynyl groups as defined above optionally substituted through any available carbon atom(s) with 1 or more substituents, such as any of the substituents described for alkyl or aryl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cyclohexadienyl, and cycloheptadienyl, which may be optionally substituted as defined for cycloalkyl. As defined and claimed herein, the term "cycloalkenyl" includes cycloalkenyl groups as defined above optionally substituted through any available carbon atom(s) with 1 or more substituents, such as any of the substituents described for alkyl or aryl.

The term "halogen" or "halo" as used herein alone or as part of another group refers to chlorine, bromine, fluorine, and iodine as well as $CF_3$, with chlorine or bromine being preferred.

The term "alkanoyl" as employed herein alone or as part of another group is alkyl linked to a carbonyl group.

The term "aroyl" as employed herein alone or as part of another group is aryl linked to a carbonyl group.

Unless otherwise indicated, the terms "alkoxy", "aryloxy" or "heteroaryloxy" as employed herein alone or as part of another group includes any of the above alkyl, aryl or heteroaryl groups linked thorough an oxygen atom.

The term "cyano," as used herein, refers to a —CN group.

The term "arylalkyl" and "heteroarylalkyl" as employed herein alone or as part of another group refer to alkyl groups as described above having an aryl or heteroaryl substituent. Representative examples of arylalkyl include, but are not limited to, benzyl, 2-phenylethyl, 3-phenylpropyl.

Unless otherwise indicated, the terms "arylalkoxy" and "cycloalkoxy" as employed herein alone or as part of another group include and aryl cycloalkyl groups linked thorough an oxygen atom.

The term "carboxylic acid" or "carboxyl", as used herein, refers to a —COOH group.

The term "benzyl" as used herein refers to —$CH_2C_6H_5$, which may optionally be substituted as defined above for alkyl.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The compounds of formula I may also have prodrug forms. Any compound that will be converted in vivo to provide the bioactive agent (i.e., the compound of formula I) is a prodrug within the scope and spirit of the invention.

Various forms of prodrugs are well known in the art. A comprehensive description of prodrugs and prodrug derivatives may be found in:

a) *The Practice of Medicinal Chemistry*, Camille G. Wermuth et al., Ch 31, (Academic Press, 1996);
b) *Design of Prodrugs*, edited by H. Bundgaard, (Elsevier, 1985); and
c) *A Textbook of Drug Design and Development*, P. Krogsgaard-Larson and H. Bundgaard, eds. Ch 5, pgs 113-191 (Harwood Academic Publishers, 1991).

Said references are incorporated herein by reference.

Embodiments of prodrugs suitable for use in the present invention include lower alkyl esters, such as ethyl ester, or acyloxyalkyl esters such as pivaloyloxymethyl (POM). For example, such esters both serve as suitable prodrugs for the carboxylic acid examples of compounds of formula I (for example, a prodrug is exemplified by compounds of formula in which R13=—COOR, where R is alkyl) and as prodrugs which mask the free phenolic hydroxyl group present in the general structure, formula I, as depicted in the structure below where the prodrug aroyl or alkanoyl group is the moiety, R—CO—, in which R is alkyl or aryl.

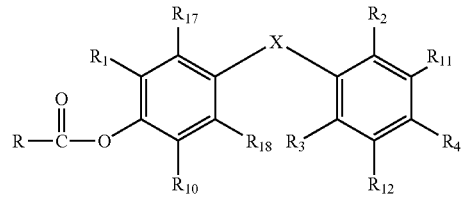

Furthermore, embodiments of prodrugs suitable for masking the phenolic hydroxyl group discussed above include phenolic alkyl ethers, such as depicted in the structure below where R=alkyl. Metabolic hydroxylation of the carbon of the alkyl group R that is attached to the phenolic oxygen leads to an intermediate capable of further decomposition to release the free phenol form of the general compounds of formula I.

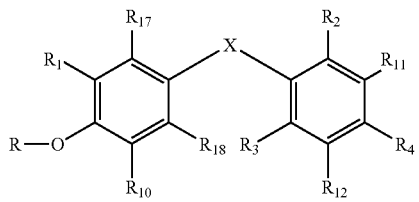

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I of the invention can be prepared as shown in the following reaction schemes and description thereof, as well as by relevant published literature procedures that may be used by one skilled in the art. Exemplary reagents and procedures for these reactions appear hereinafter and in the working Examples. Protection and deprotection in the Schemes below may be carried out by procedures generally known in the art. For example, see T. W. Greene & P. G. M. Wuts, "*Protecting Groups in Organic Synthesis*", 3$^{rd}$ Edition, (Wiley, 1999), incorporated herein by reference.

SCHEME 1

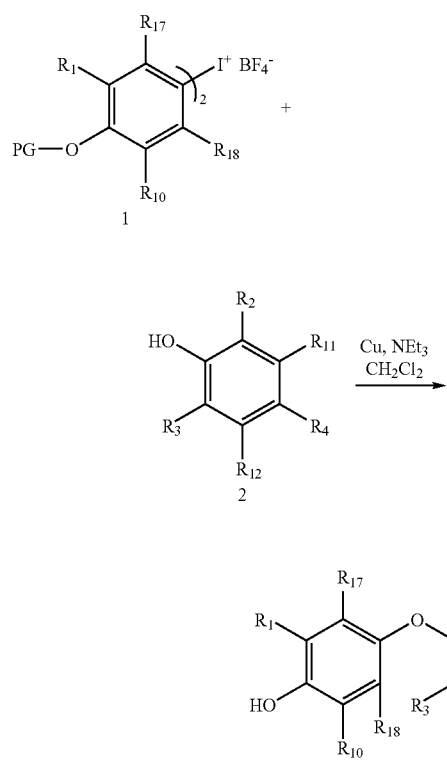

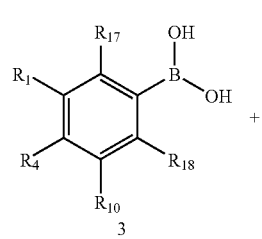

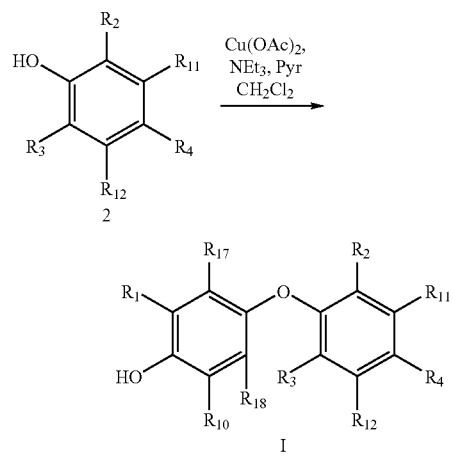

The iodonium salt (general synthetic intermediate 1) methodology depicted in Scheme 1 is amply described in the literature for the synthesis of thyroid hormone analogs ("Novel Thyroid Receptor Ligands and Methods, Y.-L. Li, Y. Liu, A. Hedfors, J. Malm, C. Mellin, M. Zhang, PCT Int. App. WO 9900353 A1 990107; D. M. B. Hickey et al., J. Chem. Soc. Perkin Trans. I, 3103-3111, 1988; N. Yokoyama et al., J. Med. Chem., 38, 695-707, 1995), and to diaryl ethers in general (E. A. Couladouros, V. I. Moutsos, Tetrahedron Lett., 40, 7023-7026, 1999).

The use of a boronic acid mediated coupling reaction (general synthetic intermediate 3) depicted in Scheme 1 is described by D. A. Evans et al. (in Tetrahedron Lett., 39, 2937-2940, 1998).

Further general means for synthesizing compounds of formula I are described in the literature (for X=O: D. M. B. Hickey et al., J. Chem. Soc. Perkin Trans. I, 3097-3102, 1988; Z.-W. Guo et al., J. Org. Chem., 62, 6700-6701, 1997; D. M. T. Chan et al., Tetrahedron Lett., 39, 2933-2936, 1998; G. M. Salamonczyk et al., Tetrahedron Lett., 38, 6965-6968, 1997; J.-F. Marcoux, J. Am. Chem. Soc., 119, 10539-10540, 1997; A. V. Kalinin et al., J. Org. Chem., 64, 2986-2987, 1999; for X=S: C. R. Harrington, Biochem. J., 43, 434-437, 1948; A. Dibbo et al., J. Chem. Soc., 2890-2902, 1961; N. Yokoyama et al., U.S. Pat. No. 5,401,772, 1995; for X=S or $SO_2$: J. L. Stanton et al., Bioorgan. Med. Chem. Letters, 10, 1661, 2000; for X=$CH_2$: L. Horner, H. H. G. Medem, Chem. Ber., 85, 520-530, 1952; G. Chiellini et al., Chemistry & Biology, 5, 299-306, 1998).

SCHEME 2

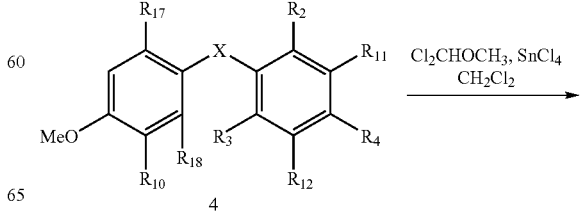

-continued

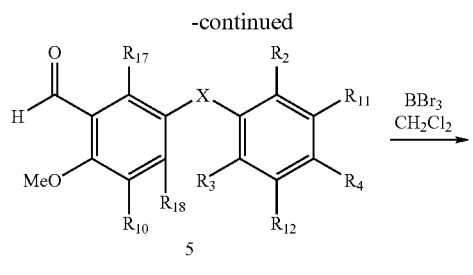

SCHEME 3

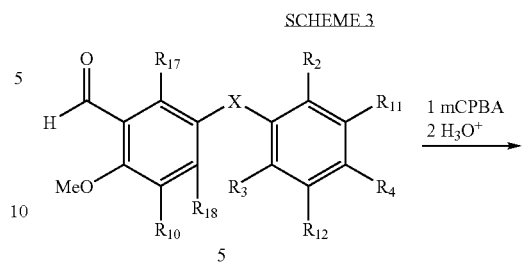

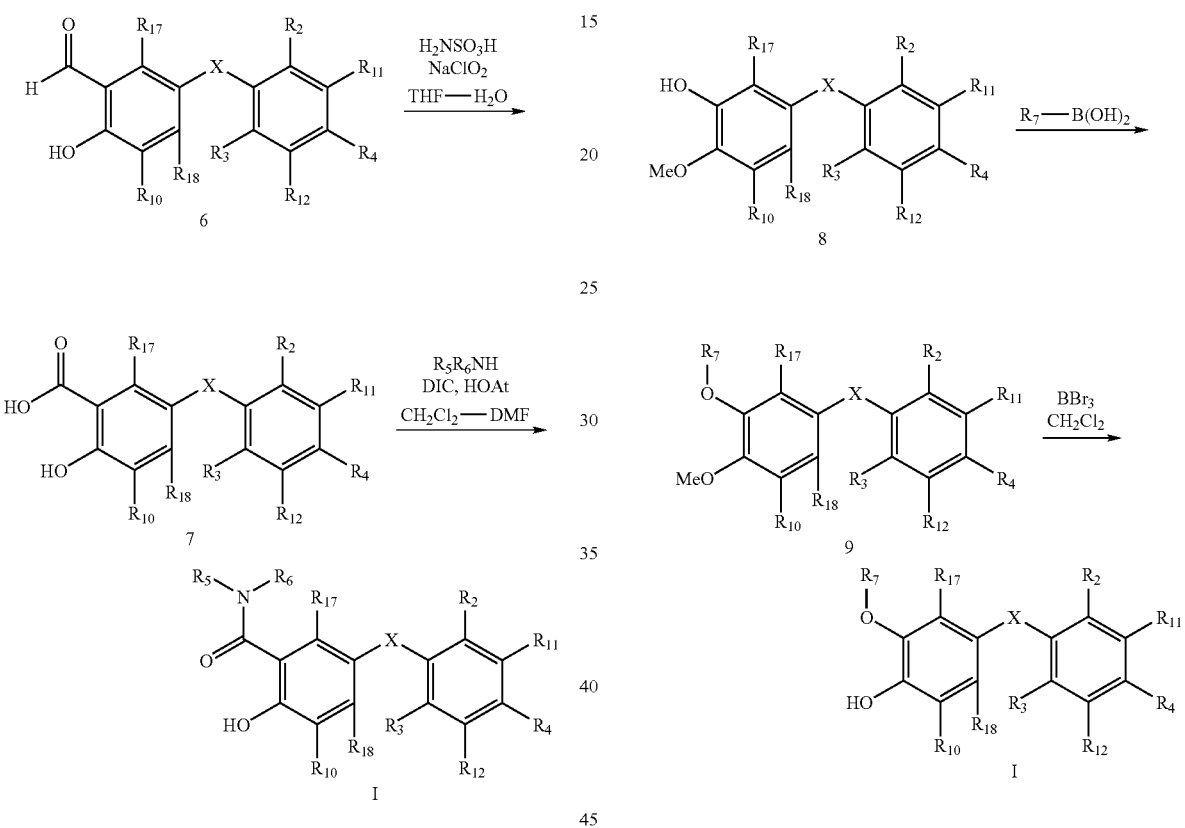

Scheme 2 describes further methodology for the preparation of carboxamide-substituted examples of compounds of formula I wherein
R1 is

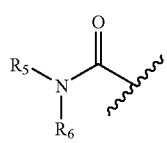

The general intermediate 4 is formylated to provide aldehyde 5, which is demethylated to afford phenol 6. Oxidation of the aldehyde gives the carboxylic acid intermediate 7, which is then converted to I in which R1 is a carboxamide group. The reaction conditions shown in Scheme 2 are representative of procedures well known to those skilled in the art.

Scheme 3 describes further methodology for the preparation of aryl ether-substituted examples of compounds of formula I wherein
R1 is

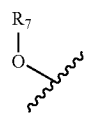

The general aldehyde intermediate 5 is treated with meta-chloroperbenzoic acid (mCPBA) to provide phenol 8 (the Baeyer-Villager reaction). The phenol 8 is coupled with an aryl boronic acid ($R_7$—$B(OH)_2$) to give intermediate 9 (D. A. Evans et al. (in Tetrahedron Lett., 39, 2937-2940, 1998). Removal of the methyl ether protecting group using $BBr_3$ yields the aryl ether substituted example of I. The reaction conditions shown in Scheme 3 are representative of procedures well known to those skilled in the art.

SCHEME 4

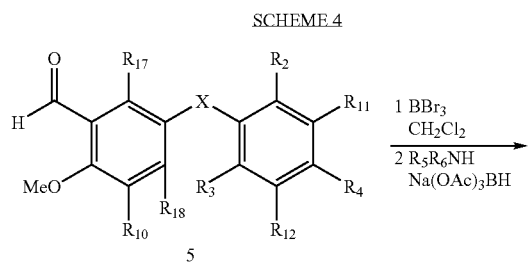

Scheme 4 describes further methodology for the preparation of examples of compounds of formula I wherein
R1 is

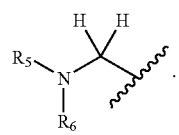

The general aldehyde intermediate 5 is first treated with boron tribromide to provide the free phenol which is then reacted with the appropriate amine in a reductive amination reaction using a reducing agent such as sodium triacetoxy-borohydride. The reaction conditions shown in Scheme 4 are representative of procedures well known to those skilled in the art.

SCHEME 5

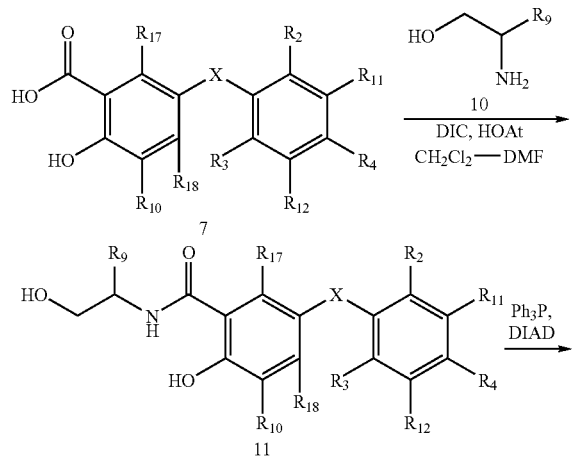

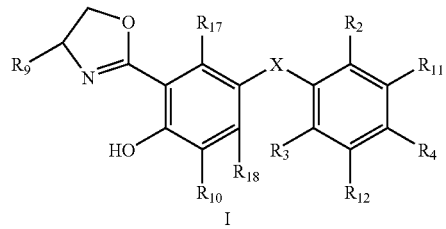

Scheme 5 describes further methodology for the preparation of examples of compounds of formula I wherein
R1 is

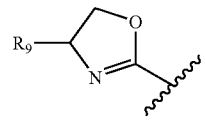

The carboxylic acid intermediate 7 is coupled with an amino alcohol intermediate of structure 10 and the resulting amide 11 is cyclized to the oxazoline analog I.

SCHEME 6

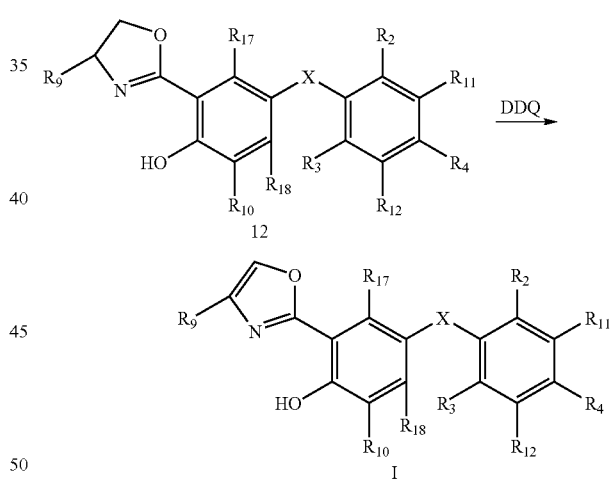

Scheme 6 describes further methodology for the preparation of examples of compounds of formula I wherein
R1 is

in which R8 is the heteroaryl group, oxazole. The oxazoline intermediate 12 prepared as described in Scheme 5 is converted using DDQ (2,3-dichloro-5,6-dicyano-1,4-benzoquinone) to the oxazole analog I.

SCHEME 7

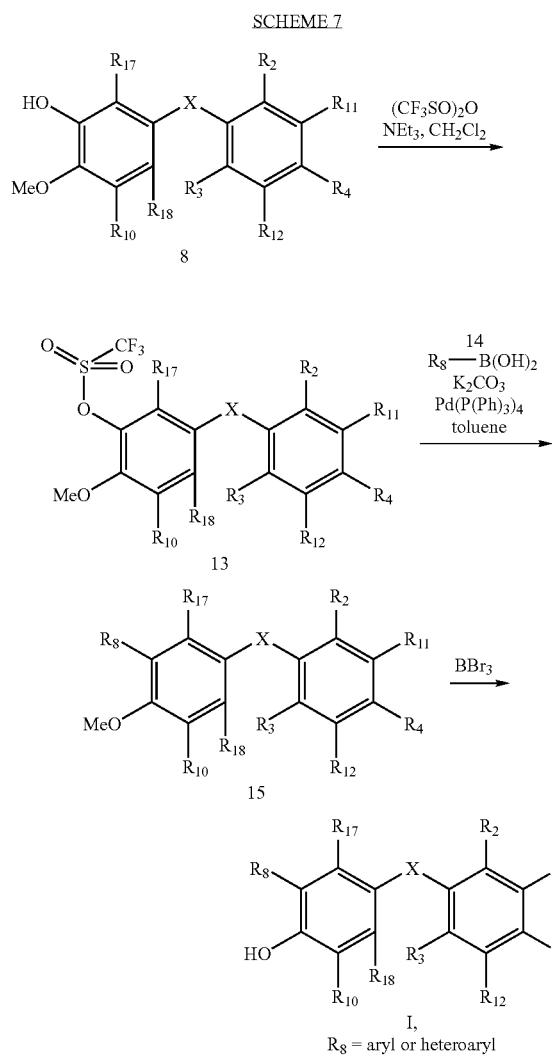

Scheme 7 describes methodology for the preparation of examples of compounds of formula I wherein R1 is

in which R8 can be aryl or heteroaryl examples provided by the use of the corresponding aryl or heteroaryl boronic acids. In this approach, the previously described intermediate 8 is converted to the corresponding triflate 13 by treatment with triflic anhydride and triethylamine. Aryl triflate 13 is coupled with an aryl boronic acid 14 using a palladium catalyst such as palladium tetrakis-triphenylphosphine and a base such as potassium carbonate to give the coupled product 15. Removal of the methyl ether protecting group using boron tribromide gives aryl or heteroaryl substituted examples of I. Alternatively, the aryl triflate intermediate 13 can be substituted by the corresponding aryl bromide 16 described in Scheme 8.

SCHEME 8

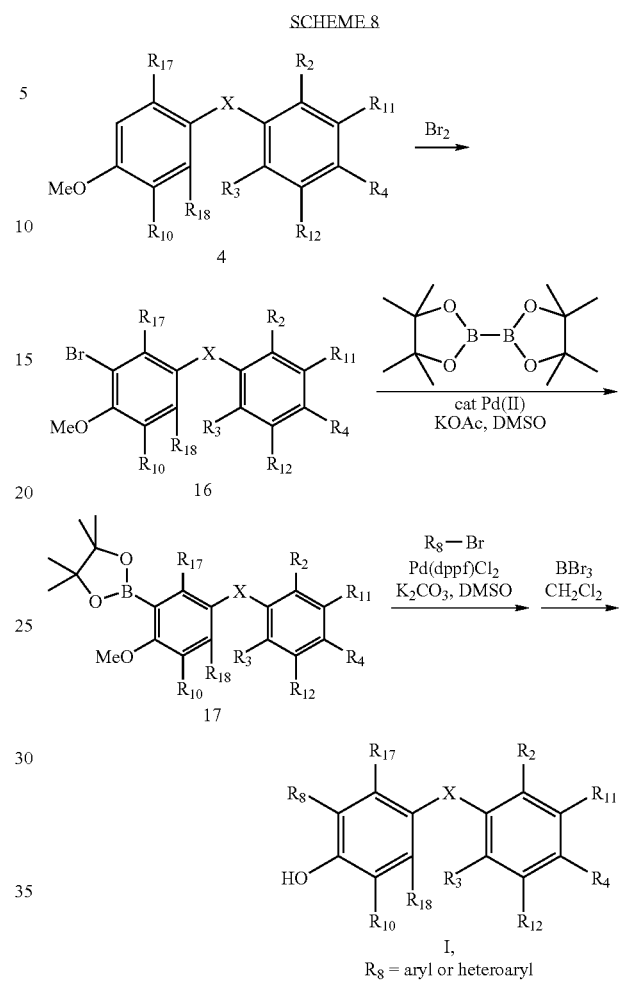

Scheme 8 describes further methodology for the preparation of examples of compounds of formula I wherein R1 is

in which R8 can be aryl or heteroaryl examples. In this approach, the previously described intermediate 4 is brominated by standard means such as treatment with molecular bromine in methylene chloride. The resulting aryl bromide 16 is reacted with bis(pinacolato)-diboron and potassium acetate in the presence of catalytic amounts of [1,1'-bis(diphenylphosphino)ferrocene]-chloropalladium(II):methylene chloride complex to give the pinacol boronate ester 17.

SCHEME 9

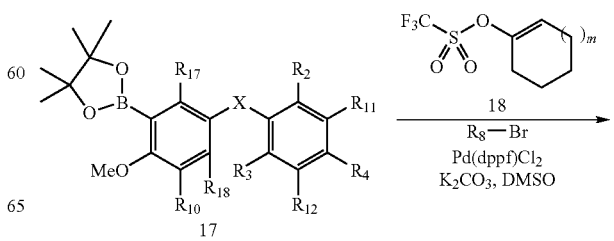

-continued

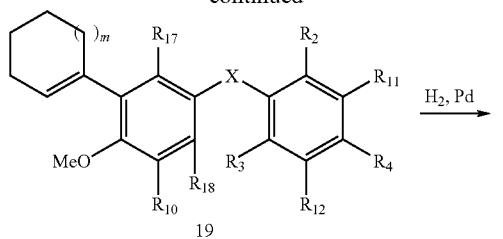

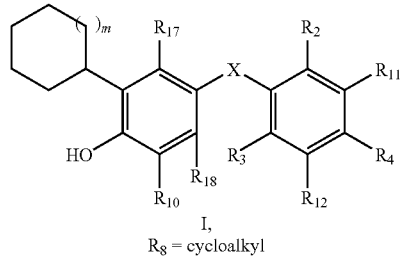

Scheme 9 describes methodology for the synthesis of compounds of formula I in which the R4 position is substituted by a cycloalkyl ring (R8=cycloalkyl). The previously described pinacol boronate ester 17 is coupled with a cycloalkenyl triflate 18 using a palladium catalyst such as [1,1'-bis(diphenylphosphino)ferrocene]-chloropalladium(II):methylene chloride complex to give the intermediate 19. Reduction of the cycloalkene double bond affords examples of compounds of formula I in which R4 is a cycloalkyl group.

SCHEME 10

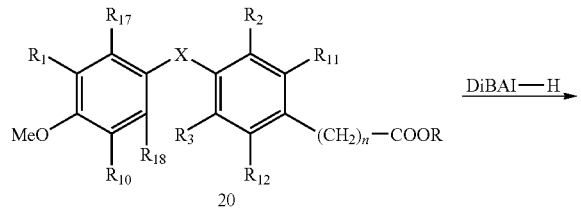

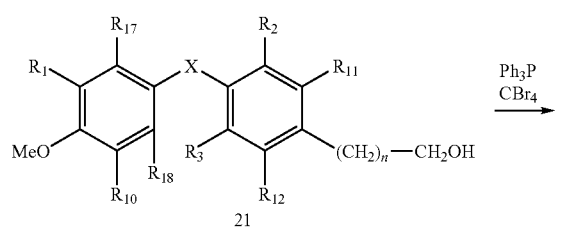

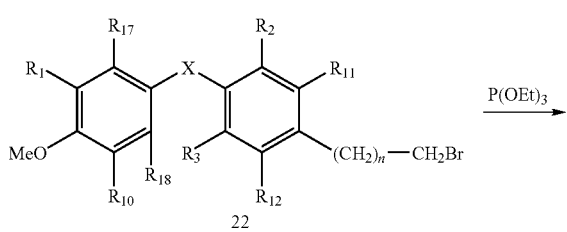

-continued

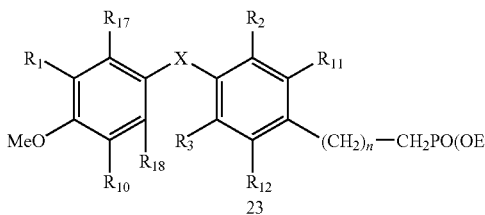

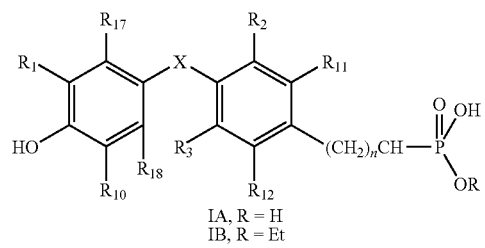

Scheme 10 describes methodology for the synthesis of compounds of formula I in which R4 is

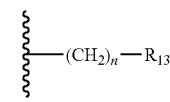

and R13 is either a phosphonic acid or phosphonic monoester. Intermediate carboxylic acid ester 20, whose synthesis follows from the schemes described above, is reduced to alcohol 21 using a reagent such as diisobutylaluminum hydride. Compound 21 is converted to the corresponding bromide 22, then heated with a trialkyl phosphite, such as triethyl phosphite to provide the phosphonic acid diester intermediate 23. Use of appropriate reaction conditions known to those skilled in the art provide either the desired phosphonic acid (IA) or phosphonic acid, monoester (IB).

SCHEME 11

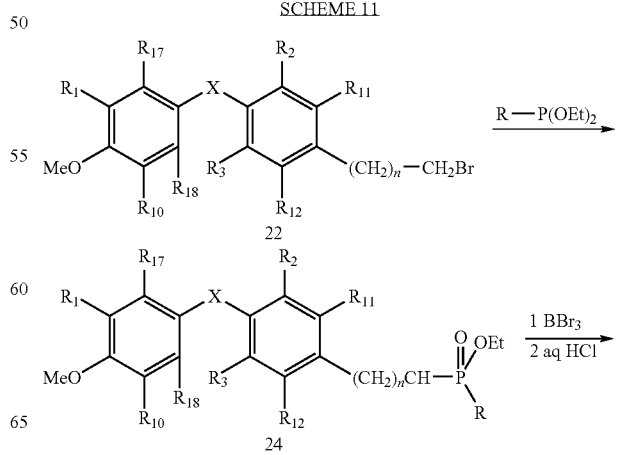

-continued

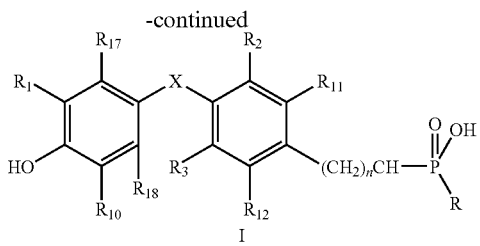

Scheme 11 describes methodology for the synthesis of compounds of formula I in which R4 is

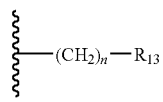

and R13 is a phosphinic acid. Bromo intermediate 22 is reacted with diethyl methylphosphonite to give the phosphinic ester 24. Treatment of intermediate 24 with boron tribromide removes the phenolic methyl ether group, and acid hydrolysis provides the desired compounds of formula I in which the R4 group is a phosphinic acid.

SCHEME 12

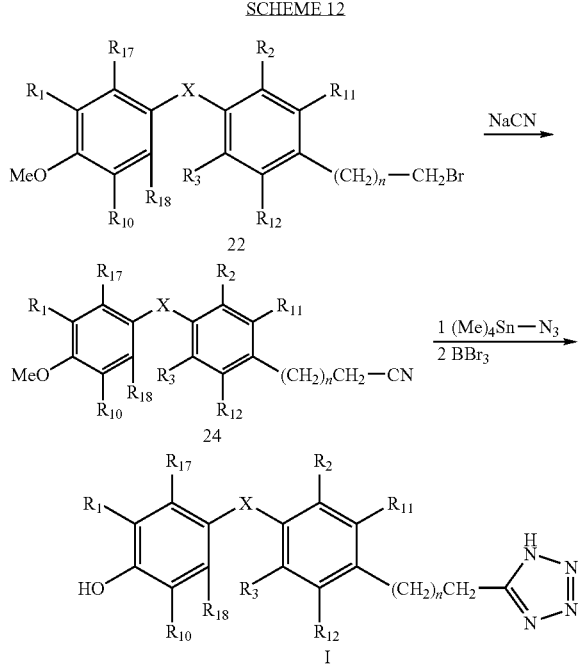

Scheme 12 describes methodology for the synthesis of compounds of formula I in which R4 is

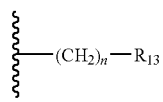

and R13 is a tetrazole. Bromo intermediate 22 is treated with sodium cyanide to give nitrile intermediate 25. Reaction of intermediate 25 with a tetraalkyltin reagent such as tetramethyltin azide converts the nitrile group to a tetrazole. Subsequent treatment with an acid such as boron tribromide removes the phenolic methyl ether group and affords the desired tetrazole compound of formula I.

It is contemplated that related variations of the above schemes can be devised by appropriate use of different protecting groups (for example, such as methyl and benzyl esters and ethers that are readily removed by acidolytic cleavage, saponification or hydrogenolysis) by those who are normally skilled in the art. For example, explicitly designated protecting groups in the above schemes may be substituted by other compatible protecting groups whose selection can be made by those who are normally skilled in the art.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods. For example, chromatographic or fractional crystallization.

Utilities & Combinations

A. Utilities

The compounds of the present invention are thyroid receptor ligands, and include compounds which are, for example, selective agonists, partial agonists, antagonists or partial antagonists of the thyroid receptor. Preferably compounds of the present invention possess activity as agonists of the thyroid receptor, and may be used in the treatment of diseases or disorders associated with thyroid receptor activity. In particular, compounds of the present invention may be used in the treatment of diseases or disorders associated with metabolic dysfunction or which are dependent upon the expression of a $T_3$ regulated gene.

Accordingly, the compounds of the present invention can be administered to mammals, preferably humans, for the treatment of a variety of conditions and disorders, including, but not limited to hypothyroidism; subclinical hyperthyroidism; non-toxic goiter; atherosclerosis; thyroid hormone replacement therapy (e.g., in the elderly); malignant tumor cells containing the thyroid receptor; papillary or follicular cancer; maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); accelerating healing of complicated fractures, e.g. distraction osteogenesis; in joint replacement; eating disorders (e.g., anorexia); treatment of obesity and growth retardation associated with obesity; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of hyperinsulinemia; stimulation of osteoblasts, bone remodeling and cartilage growth; regulation of food intake; treatment of insulin resistance, including NIDDM, in mammals (e.g., humans); treatment of insulin resistance in the heart; treatment of congestive heart failure; treatment of musculoskeletal impairment (e.g., in the elderly); improvement of the overall pulmonary function; skin disorders or diseases, such as glucocorticoid induced dermal atrophy, including restoration of dermal atrophy induced by topical glucocorticoids, and the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, dermal atrophy induced by aging (wrinkles, etc.), wound healing, keloids, stria, cellulite, roughened skin, actinic skin damage, lichen planus, ichtyosis, acne, psoriasis, Demier's disease, eczema, atopic dermatitis, chloracne, pityriasis and skin scarring.

The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other modulators and/or ligands of the thyroid receptor or other suitable therapeutic agents useful in the treatment of the aforementioned disorders including: anti-diabetic agents; anti-osteoporosis agents; anti-obesity agents; growth promoting agents (including growth hormone secretagogues); anti-inflammatory agents; anti-anxiety agents; anti-depressants; anti-hypertensive agents; cardiac glycosides; cholesterol/lipid lowering agents; appetite suppressants; bone resorption inhibitors; thyroid mimetics (including other thyroid receptor agonists); anabolic agents; and anti-tumor agents.

Examples of suitable anti-diabetic agents for use in combination with the compounds of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2), glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-obesity agents for use in combination with the compounds of the present invention include aP2 inhibitors, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), other thyroid receptor beta drugs, such as a thyroid receptor ligand as disclosed in WO 97/21993 (U. Cal SF), WO 99/00353 (KaroBio) and GB98/284425 (KaroBio), a cannabinoid-1 receptor antagonist, such as SR-141716 (Sanofi) and/or an anorectic agent, such as dexamphetamine, phentermine, phenylpropanolamine or mazindol.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin $5\text{-HT}_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

A further use of the compounds of this invention is in combination with steriodal or non-steroidal progesterone receptor agonists ("PRA"), such as levonorgestrel, medroxyprogesterone acetate (MPA).

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

For the treatment of skin disorders or diseases as described above, the compounds of the present invention may be used alone or optionally in combination with a retinoid, such as tretinoin, or a vitamin D analog.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors, squalene synthetase inhibitors, fibrates, bile acid sequestrants, ACAT inhibitors, MTP inhibitors, lipooxygenase inhibitors, an ileal Na$^+$/bile acid cotransporter inhibitor, cholesterol absorption inhibitors, and cholesterol ester transfer protein inhibitors (e.g., CP-529414).

MTP inhibitors which may be employed herein in combination with one or more compounds of formula I include MTP inhibitors as disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440 all incorporated herein by reference.

The HMG CoA reductase inhibitors which may be employed in combination with one or more compounds of formula I include mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Further HMG CoA reductase inhibitors which may be employed herein include fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499, 289, keto analogs of mevinolin (lovastatin), as disclosed in European Patent Application No. 0,142,146 A2, as well as other known HMG CoA reductase inhibitors.

The squalene synthetase inhibitors which may be used in combination with the compounds of the present invention include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinylmethyl)phosphonates, terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

Bile acid sequestrants which may be used in combination with the compounds of the present invention include cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

ACAT inhibitors suitable for use in combination with compounds of the invention include ACAT inhibitors as described in, Drugs of the Future 24, 9-15 (1999), (Avasimibe); "The ACAT inhibitor, Cl-011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, Cardiovasc.

Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62.

Examples of suitable cholesterol absorption inhibitor for use in combination with the compounds of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425-430 (1999).

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

The aforementioned patents and patent applications are incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with a hypolypidemic agent, an antidepressant, a bone resorption inhibitor and/or an appetite suppressant, the compounds of formula I may be employed in a weight ratio to the additional agent within the range from about 500:1 to about 0.005:1, preferably from about 300:1 to about 0.01:1.

Where the antidiabetic agent is a biguanide, the compounds of formula I may be employed in a weight ratio to biguanide within the range from about 0.01:1 to about 100:1, preferably from about 0.5:1 to about 2:1.

The compounds of formula I may be employed in a weight ratio to a glucosidase inhibitor within the range from about 0.01:1 to about 100:1, preferably from about 0.5:1 to about 50:1.

The compounds of formula I may be employed in a weight ratio to a sulfonylurea in the range from about 0.01:1 to about 100:1, preferably from about 0.2:1 to about 10:1.

The compounds of formula I may be employed in a weight ratio to a thiazolidinedione in an amount within the range from about 0.01:1 to about 100:1, preferably from about 0.5:1 to about 5:1. The thiazolidinedione may be employed in amounts within the range from about 0.01 to about 2000 mg/day, which may optionally be administered in single or divided doses of one to four times per day.

Further, where the sulfonylurea and thiazolidinedione are to be administered orally in an amount of less than about 150 mg, these additional agents may be incorporated into a combined single tablet with a therapeutically effective amount of the compounds of formula I.

Metformin, or salt thereof, may be employed with the compounds of formula I in amounts within the range from about 500 to about 2000 mg per day, which may be administered in single or divided doses one to four times daily.

The compounds of formula I may be employed in a weight ratio to a PPAR-alpha agonist, a PPAR-gamma agonist, a PPAR-alpha/gamma dual agonist, an SGLT2 inhibitor and/or an aP2 inhibitor within the range from about 0.01:1 to about 100:1, preferably from about 0.5:1 to about 5:1.

An MTP inhibitor may be administered orally with the compounds of formula I in an amount within the range of from about 0.01 mg/kg to about 100 mg/kg and preferably from about 0.1 mg/kg to about 75 mg/kg, one to four times daily.

A preferred oral dosage form, such as tablets or capsules, may contain the MTP inhibitor in an amount of from about 1 to about 500 mg, preferably from about 2 to about 400 mg, and more preferably from about 5 to about 250 mg, administered on a regimen of one to four times daily.

For parenteral administration, the MTP inhibitor may be employed in an amount within the range of from about 0.005 mg/kg to about 10 mg/kg and preferably from about 0.005 mg/kg to about 8 mg/kg, administered on a regimen of one to four times daily.

A HMG CoA reductase inhibitor may be administered orally with the compounds of formula I within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A squalene synthetase inhibitor may be administered with the compounds of formula I within the range of from about 10 mg to about 2000 mg and preferably from about 25 mg to about 200 mg.

A preferred oral dosage form, such as tablets or capsules, will contain the squalene synthetase inhibitor in an amount of from about 10 to about 500 mg, preferably from about 25 to about 200 mg.

The compounds of formula I of the invention can be administered orally or parenterally, such as subcutaneously or intravenously, as well as by nasal application, rectally or sublingually to various mammalian species known to be subject to such maladies, e.g., humans, in an effective amount within the dosage range of abut 0.01 µg/kg to about 1000 µg/kg, preferably about 0.1 µg/kg to 100 µg/kg, more preferably about 0.2 µg/kg to about 50 µg/kg (or form about 0.5 to 2500 mg, preferably from about 1 to 2000 mg) in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

EXAMPLES

The following working Examples serve to better illustrate, but not limit, some of the preferred embodiments of the present invention.

Example 1

[3,5-Dibromo-4-(4-hydroxy-3-phenethylcarbamoyl-phenoxy)-phenyl]-acetic Acid

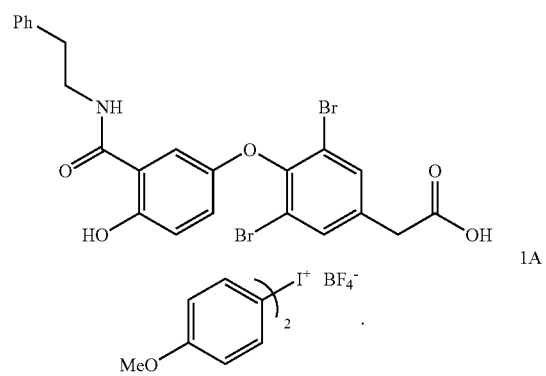

Nitric acid (fuming, 100% reagent, 10.4 mL) was added dropwise to acetic anhydride (14.4 mL) while keeping the solution temperature between −20° C. and −25° C. (ethanol/dry ice bath). Iodine (4.84 g, 0.191 mol) was added in one portion followed by the dropwise addition of trifluoroacetic acid (17.8 mL) while keeping the reaction mixture between −20° C. and −25° C. Upon completion of addition, the reaction was stirred at room temperature until all the iodine had dissolved. The nitrogen oxides were then purged with nitrogen gas and the resulting mixture concentrated by short-path vacuum distillation while taking care to keep the bath temperature below 40° C. The light yellow solid residue that resulted was partially dissolved in 54 mL of acetic anhydride. The resulting slurry was treated sequentially by the dropwise addition of anisole (5.8 g, 0.053 mol) dissolved in 65 mL of acetic anhydride and trifluoroacetic acid (10 mL), while keeping the temperature between −20° C. and −25° C. The reaction mixture was stirred at room temperature overnight, then concentrated again by short-path vacuum distillation while taking care to keep the bath temperature below 40° C., and finally treated with 56 mL of methanol. The resulting mixture was poured into a solution comprised of 52 mL of 10% NaHSO-3 and 360 mL of 2M NaBF4. After stirring this mixture vigorously for 2 hr, the aqueous portion was decanted and the remaining semi-solid was washed with several portions of hexane. Filtration followed by drying in vacuo afforded 4.6 g of bis-(4-methoxyphenyl)iodonium tetrafluoroborate (1A) as a light yellow solid (satisfactory 1H and 13C NMR were obtained).

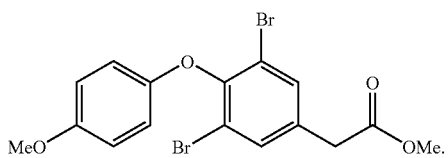

Bis-(4-methoxyphenyl)iodonium tetrafluoroborate (1A, 2 g, 4.67 mmol) and copper bronze (0.59 g, 9.3 mmol) were suspended in 30 mL of CH2Cl2 under argon, cooled in an ice-bath, and treated with a solution of triethylamine (0.472 g, 4.66 mmol) and methyl 3,5-dibromo-4-hydroxyphenylacetate (1.51 g, 4.67 mmol) in 15 mL of CH2Cl2, added dropwise. After 30 minutes, the ice-bath was removed and the reaction kept at room temperature overnight. The reaction mixture was concentrated in vacuo, then directly purified by flash chromatography (silica gel, 7.5% ethyl acetate in hexanes) to give 1.42 g (75%) of the desired diaryl ether coupling product, Compound 1B (satisfactory 1H and 13C NMR were obtained).

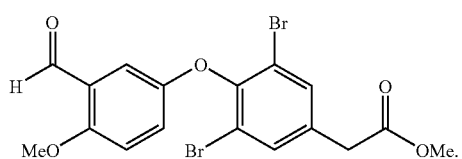

To a solution of compound 1B (1.41 g, 3.6 mmol) in 20 mL of CH2Cl2 cooled to −60° C. under nitrogen was added dichloromethyl methyl ether (0.65 mL, 7.2 mmol) followed by stannic chloride (21 mL of 1M in CH2Cl2). The reaction was kept between −60° C. and −10° C. for 4 hours, then for 2 hours between −10° C. and 0° C. The reaction was next quenched by the addition of 2N aqueous HCl, stirred vigorously for 20 minutes, then extracted with CH2Cl2. The combined organic extract was washed with saturated NaHCO3 solution and water, then dried over Na2SO4. The crude product mixture was redissolved in methanol, and the resulting solution was kept at room temperature overnight. After removal of the methanol in vacuo, flash chromatography (silica gel, ethyl acetate/hexane) gave 1.4 g (85%) of the desired aldehyde product, Compound 1C (satisfactory 1H and 13C NMR were obtained).

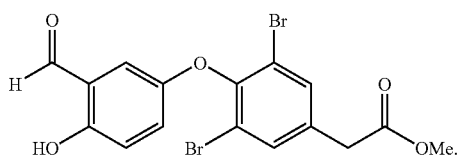

To a solution containing boron tribromide (6.2 g, 24.8 mmol) in 12 mL of CH2Cl2 cooled to −68° C. under nitrogen was added dropwise Compound 1C (1.1 g, 2.48 mmol) dissolved in 12 mL of CH2Cl2. After removal of the cooling bath, the reaction was allowed to warm to 0° C., then kept at that temperature for 1 hour. The reaction mixture was then cooled back down to −20° C., then quenched by the dropwise addition of 7 mL of water. Next the reaction mixture was repeatedly diluted with methanol and concentrated in vacuo, then treated with CH2Cl2 and water. The organic extract was washed with water, saturated NaHCO3 and brine, then dried over Na2SO4 and concentrated in vacuo to provide 1.02 g of crude demethylated product, Compound 1D, as a light yellow solid (satisfactory 1H and 13C NMR were obtained). This material was used as such in the next reaction.

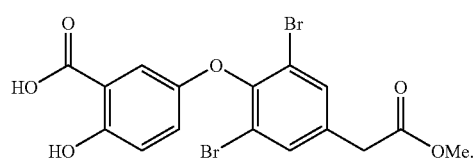

To a solution of Compound 1D (239 mg, 0.54 mmol) in 3.75 mL of 2:1 tetrahydrofuran/water cooled in an ice-bath was added dropwise sulfamic acid (1 mL of aqueous 1M), followed by the dropwise addition of a solution of sodium chlorite (98 mg, 1.08 mmol) dissolved in 1.1 mL of water. The slightly exothermic reaction was stirred in an ice-bath for 2 hours, then diluted with 20 mL of water and extracted with CH2Cl2. The combined organic extract was washed with water and brine, then dried over MgSO4, filtered and concentrated in vacuo to give 0.235 g of carboxylic acid product, Compound 1E, as a white solid (satisfactory 1H and 13C NMR were obtained). This material was used without purification in the next reaction.

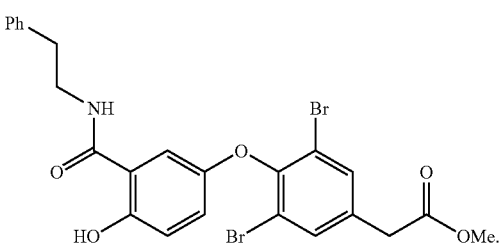

Compound 1E (60 mg, 0.13 mmol), HOAt (27.2 mg, 0.2 mmol) and phenethylamine (17.4 mg, 0.14 mmol) were dissolved in a mixture of 0.3 mL of CH2Cl2 and 0.1 mL of DMF. Diisopropylcarbodiimide (21.4 mg, 0.2 mmol) was added to the reaction at room temperature and the reaction was stirred for an additional 2 hours, then directly flash chromatographed (silica gel, 1:9 ethyl acetate/hexane) to yield 61 mg (84%) of the desired amide product, Compound 1F (satisfactory 1H and 13C NMR were obtained).

Example 1

Compound 1F (26.6 mg, 0.0474 mmol) was treated with a mixture of 0.1 mL of methanol and 0.1 mL of 1N aqueous sodium hydroxide solution. The reaction was stirred at 35° C. for 2 hours, then acidified with 0.12 mL of 1N aqueous hydrochloric acid and extracted with ethyl acetate. The organic extract was washed with brine, dried over Na2SO4 and concentrated in vacuo to provide 12 mg (46%) of Example 1 (HPLC purity 98.9%, satisfactory MS (550.1, [M+H]+) and 1H and 13C NMR were obtained).

Example 2

[3,5-Dichloro-4-(4-hydroxy-3-phenethylcarbamoyl-phenoxy)-phenyl]-acetic Acid

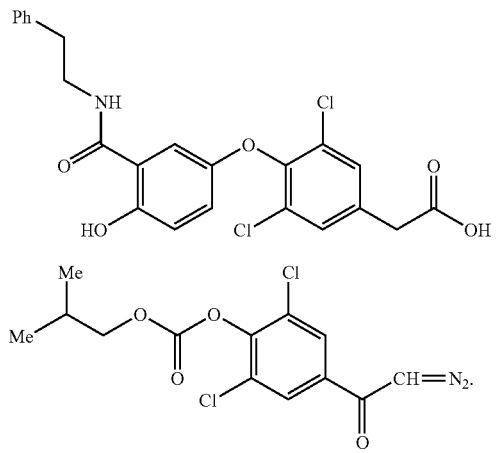

Isobutylchloroformate (30.97 mL, 234 mmol) was added to 3,5-dichloro-4-hydroxybenzoic acid (24.25 g, 117 mmol) in 250 mL of THF cooled to −20° C. Next N-methylmorpholine (25.73 mL, 234 mmol) was added slowly while maintaining the internal temperature at ca. −20° C. After 30 minutes, the reaction mixture was filtered through a glass frit and rinsed with 80 mL of THF. A diazomethane solution was prepared beforehand by the careful addition of MNNG, 1-methyl-3-nitro-1-nitrosoguanidine (50 g, 329 mmol) to a rapidly stirred mixture of 40% aq NaOH (150 mL) and diethyl ether (500 mL) cooled in an ice-water bath. The yellow ethereal diazomethane solution was carefully decanted from the water layer and dried over KOH pellets in a chilled flask. The cold, dried ethereal diazomethane solution was added to the THF solution of mixed anhydride (above) kept at −20° C. The combined reaction mixture was kept under argon and chilled in an ice-water bath for 7 h, then purged with argon, treated with a few drops of acetic acid and extracted with ether (500 mL). The organic extract was rinsed with water, saturated NaHCO3 and brine, dried (MgSO4) and concentrated in vacuo. Trituration of the crude product with hexanes gave 25.38 g (68%) of purified Compound 2A as a solid, satisfactory 1H and 13C NMR.

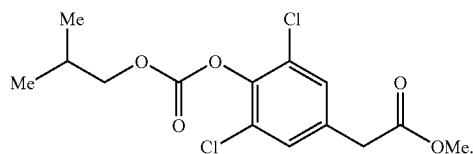

To a solution of silver benzoate (3.2 g, 14 mmol) dissolved in a mixture of 300 mL of triethylamine and 200 mL of methanol cooled in an ice-water bath was added over a period of 5-10 minutes Compound 2A (30 g, 90.59 mmol) in a mixture of 200 of methanol and 100 mL of dichloromethane. The reaction was covered from light and allowed to come to room temperature overnight, then filtered over Celite with rinsing with an additional 400 mL of methanol. The organic solution was concentrated in vacuo to 35 g of crude dark brown oil. Chromatography on 450 g of silica gel eluted with 4/1, hexanes/EtOAc yielded 20.07 g (67% yield) of Compound 2B, satisfactory 1H and 13C NMR.

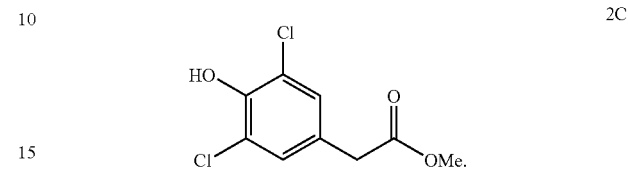

Compound 2C (20 g, 59.67 mmol) was dissolved in 18 mL of methanol and added to 100 mL of 0.5 N sodium methoxide in methanol. The reaction mixture was heated in a 60° C. bath for 3 h, then treated with an additional 25 mL of 0.5 N sodium methoxide solution. After a further 2 h, the reaction was cooled in an ice-water bath and acidified with 70 mL of 1N aq HCl, concentrated in vacuo and the precipitated product solution was refrigerated overnight, then filtered to give product contaminated with inorganic salts. The solid residue was extracted with ethyl acetate. The organic extract was rinsed with water, then brine and dried with MgSO4. Removal of solvents in vacuo provided purified Compound 2C (13.5 g, 96% yield) with satisfactory 1H and 13C NMR.

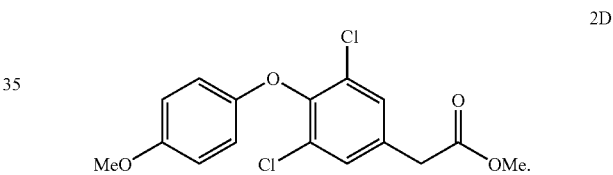

Compound 2C (145 mg, 0.426 mmol) was converted to 150 mg (80%) of product 2D (satisfactory 1H and 13C NMR were obtained) by the method described above for compound 1C.

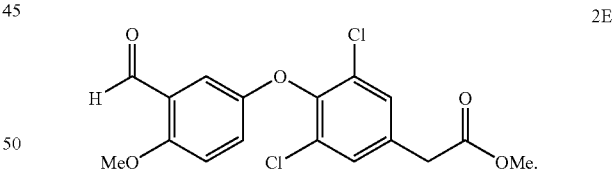

Compound 2D (120 mg, 0.325 mmol) was converted to 100 mg (86%) of crude product 2E (satisfactory 1H and 13C NMR were obtained) by the method described above for compound 1C. This material was used in the next reaction without further purification.

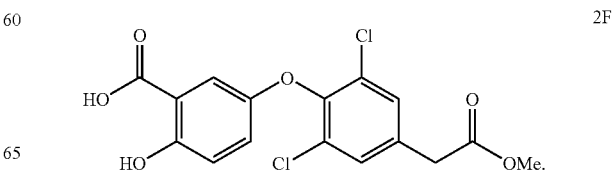

Oxidation of compound 2E (99 mg, 0.28 mmol) yielded 98 mg (86%) of crude product 2F (satisfactory 1H and 13C NMR were obtained) by the method described above for compound 1D. This material was used in the next reaction without further purification.

Coupling of phenethylamine (8.5 mg, 0.07 mmol) to compound 2F (20 mg, 0.054 mmol) by the method described above for compound 1E yielded, after purification (flash chromatography on silica gel, ethyl acetate/hexane), 25 mg (72%) of product 2G (satisfactory 1H and 13C NMR were obtained).

2G

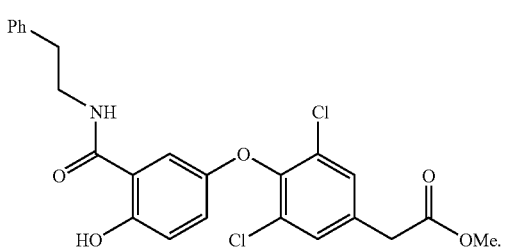

Example 2

Saponification of compound 2G (18 mg, 0.038 mmol) by the method described above for the preparation of Example 1 yielded 11 mg (64%) of the desired product, Example 2 (HPLC purity 96.1%, satisfactory MS (458.4, [M−H]$^-$) and 1H NMR were obtained)

Examples 3 to 17

By generally following the procedures of Example 1 or 2, the following compounds of the invention were prepared.

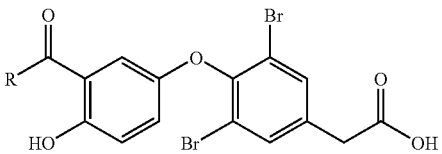

| Example | Name | R | [M + H]$^+$ |
|---|---|---|---|
| 3 | [4-(3-Benzylcarbamoyl-4-hydroxy-phenoxy)-3,5-dibromo-phenyl]-acetic acid | benzyl-NH- | 534 |
| 4 | [5-(2,6-Dibromo-4-carboxymethyl-phenoxy)-2-hydroxy-benzoylamino]-acetic acid | -NH-CH$_2$-COOH | 502.1 *M − H)$^-$ |
| 5 | [3,5-Dibromo-4-(4-hydroxy-3-phenylcarbamoyl-phenoxy)-phenyl]-acetic acid | phenyl-NH- | 505.92 |
| 6 | {3,5-Dibromo-4-[4-hydroxy-3-(4-phenyl-butylcarbamoyl)-phenoxy]-phenyl}-acetic acid | Ph-(CH$_2$)$_4$-NH- | 576 |
| 7 | {3,5-Dibromo-4-[4-hydroxy-3-(3-phenyl-propylcarbamoyl)-phenoxy]-phenyl}-acetic acid | Ph-(CH$_2$)$_3$-NH- | 562 |
| 8 | (S)-{3,5-Dibromo-4-[4-hydroxy-3-(2-hydroxy-1-phenyl-ethylcarbamoyl)-phenoxy]-phenyl}-acetic acid | (S)-PhCH(CH$_2$OH)-NH- | 563.07 [M − H]$^-$ |

-continued

| Example | Name | R | [M + H]⁺ |
|---|---|---|---|
| 9 | (R)-{3,5-Dibromo-4-[4-hydroxy-3-(2-hydroxy-1-phenyl-ethylcarbamoyl)-phenoxy]-phenyl}-acetic acid | (R)-CH(Ph)-CH₂OH linked via NH | 564 |
| 10 | (R)-{3,5-Dibromo-4-[4-hydroxy-3-(2-hydroxy-2-phenyl-ethylcarbamoyl)-phenoxy]-phenyl}-acetic acid | (R)-CH(OH)(Ph)-CH₂-NH- | 565.97 |
| 11 | (S)-{3,5-Dibromo-4-[4-hydroxy-3-(3-hydroxy-3-phenyl-propylcarbamoyl)-phenoxy]-phenyl}-acetic acid | (S)-CH(OH)(Ph)-CH₂-CH₂-NH- | 579.93 |
| 12 | (R)-{3,5-Dibromo-4-[4-hydroxy-3-(3-hydroxy-3-phenyl-propylcarbamoyl)-phenoxy]-phenyl}-acetic acid | (R)-CH(OH)(Ph)-CH₂-CH₂-NH- | Not available |
| 13 | (S)-{3,5-Dibromo-4-[4-hydroxy-3-(2-hydroxy-2-phenyl-ethylcarbamoyl)-phenoxy]-phenyl}-acetic acid | (S)-CH(OH)(Ph)-CH₂-NH- | 565.9 |
| 14 | (R)-{3,5-Dibromo-4-[4-hydroxy-3-(1-hydroxymethyl-2-methyl-propylcarbamoyl)-phenoxy]-phenyl}-acetic acid | (R)-CH(CH(Me)₂)(CH₂OH)-NH- | 532.0 |
| 15 | (S)-{3,5-Dibromo-4-[4-hydroxy-3-(1-hydroxymethyl-2-methyl-propylcarbamoyl)-phenoxy]-phenyl}-acetic acid | (S)-CH(CH(Me)₂)(CH₂OH)-NH- | 532.0 |
| 16 | (S)-{3,5-Dibromo-4-[4-hydroxy-3-(2-hydroxy-4-methyl-ethylcarbamoyl)-phenoxy]-phenyl}-acetic acid | (S)-CH(Me)(CH₂OH)-NH- | 502 |
| 17 | (R)-{3,5-Dibromo-4-[4-hydroxy-3-(2-hydroxy-1-methyl-ethylcarbamoyl)-phenoxy]-phenyl}-acetic acid | (R)-CH(Me)(CH₂OH)-NH- | 502 |

Examples 18 to 62

Examples 18 to 62 were prepared as part of solution-phase libraries using one of the following procedures:

Procedure A to Couple Monobasic Amines:

(Example 56 is described to exemplify this procedure) To a 1 dram reaction vial was added 2-chloro-6-fluorobenzylamine (13.0 mg, 0.081 mmol, 1.6 eq). A solution of HOAt (11.6 mg, 0.085 mmol, 1.7 eq) and carboxylic acid 1E (23 mg, 0.05 mmol, 1 eq) in 0.25 mL of 4:1 THF/DMF was added to the reaction vial (in the case of amine hydrochloride salts, diisopropylethylamine (30 mg, 0.23 mmol, 4.6 eq) was added). EDC (20 mg, 0.104 mmol, 2.1 eq) was then added and the reaction mixture sonicated for 1 minute. The reaction vial was shaken for 60 hours at room temperature following which a solution of LiOH.H2O (22 mg, 0.52 mmol, 10.5 eq) in 0.5 mL 1:1 MeOH/H2O was added and the mixture shaken for 12 hours.

The product was purified via solid phase extraction using a Vac Elut vacuum manifold (Varian) by the procedure outlined below:

1) Dowex-H+ (approx. 250 mg) was added to the reaction vial.

2) An 8 mL syringe fitted with a frit was placed atop a Varian C-18 2 gm cartridge (pre-equilibrated with 5 mL Solvent B (90:10:1 MeOH/H20/TFA) followed by 5 mL Solvent A (90:10:1 H2O/MeOH/TFA)).

3) The reaction mixture was diluted with 4 mL Solvent A and loaded onto the 8 mL syringe assembled as above.

4) Column was rinsed with 6 mL Solvent A; then 5 mL of 30:70:1 MeOH/H2O/TFA to remove HOAt.

5) The product was eluted with 10 mL Solvent B into a 16×100 mm tube.

The product solution was concentrated using a speed vac for 16 hours to afford 27.9 mg (95%) of Example 56 as a solid. Reverse phase analytical HPLC analysis indicated a purity of 88.4%. MS (electrospray): m/z 588 (M+H).

Procedure B to Couple Dibasic Amines in Which Only One of the Amine Groups can Undergo Acylation:

The procedure used was as above except that DIC (1.5 eq) and HOBt (1.5 eq) replaced EDC and HOAt, respectively. In the case of amine hydrochlorides, 30 mg N-methylmorpholine was added. The purification protocol was modified as below:

1) Dowex-H+ (approx. 250 mg) was added to the reaction vial.

2) An 8 mL syringe fitted with a frit was placed atop a 3 gm SCX cartridge (pre-equilibrated with 5 mL Solvent B (90:10:1 MeOH/H2O/TFA) followed by 5 mL Solvent A (90:10:1 H2O/MeOH/TFA)).

3) The reaction mixture was diluted with 4 mL Solvent A and loaded onto the 8 mL syringe assembled as above.

4) Column was rinsed with 6 mL Solvent A; 6 mL Solvent B to remove all non-basic components.

5) The product was eluted with 9 mL 2M NH3 in methanol.

The product solutions were concentrated using a speed vac for 16 hours to afford product amides. All products were further purified, if necessary, by reverse phase preparative HPLC and gave satisfactory purity (>80%) and MS.

Examples 18 to 62 described in the table below were prepared by procedure A or B described above.

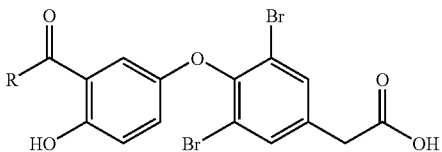

| Example | Name | R | [M + H]+ |
|---|---|---|---|
| 18 | (4-{3-[(Benzo[1,3]dioxol-5-ylmethyl)-carbamoyl]-4-hydroxy-phenoxy}-3,5-dibromo-phenyl)-acetic acid | | 579.93 |
| 19 | {3,5-Dibromo-4-[4-hydroxy-3-(indan-2-ylcarbamoyl)-phenoxy]-phenyl}-acetic acid | | 562.01 |
| 20 | {3,5-Dibromo-4-[3-(cyclohexylmethyl-carbamoyl)-4-hydroxy-phenoxy]-phenyl}-acetic acid | | 542.04 |
| 21 | (3,5-Dibromo-4-{4-hydroxy-3-[2-(4-methoxy-phenyl)-ethylcarbamoyl]-phenoxy}-phenyl)-acetic acid | | 579.98 |

-continued

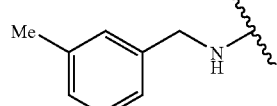

| Example | Name | R | [M + H]+ |
|---|---|---|---|
| 22 | {3,5-Dibromo-4-[4-hydroxy-3-(3-methyl-benzylcarbamoyl)-phenoxy]-phenyl}-acetic acid | 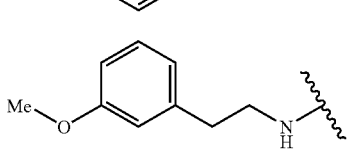 | 610.01 |
| 23 | (3,5-Dibromo-4-{4-hydroxy-3-[2-(3-methoxy-phenyl)-ethylcarbamoyl]-phenoxy}-phenyl)-acetic acid | 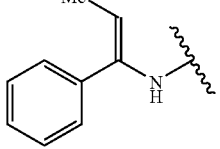 | 579.98 |
| 24 | (R)-{3,5-Dibromo-4-[4-hydroxy-3-(1-phenyl-propylcarbamoyl)-phenoxy]-phenyl}-acetic acid | 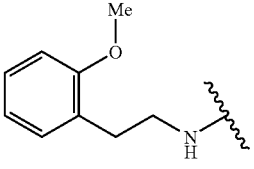 | 563.99 |
| 25 | (3,5-Dibromo-4-{4-hydroxy-3-[2-(2-methoxy-phenyl)-ethylcarbamoyl]-phenoxy}-phenyl)-acetic acid | 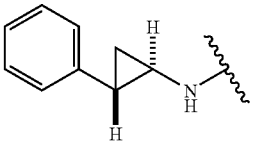 | 579.97 |
| 26, racemic | {3,5-Dibromo-4-[4-hydroxy-3-(2-phenyl-cyclopropylcarbamoyl)-phenoxy]-phenyl}-acetic acid (racemic, trans) | 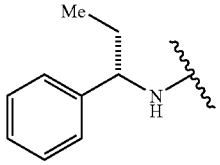 | 561.96 |
| 27 | (S)-{3,5-Dibromo-4-[4-hydroxy-3-(1-phenyl-propylcarbamoyl)-phenoxy]-phenyl 1-acetic acid | 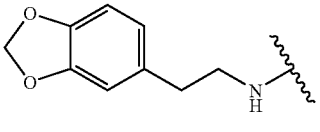 | 564.02 |
| 28 | {4-[3-(2-Benzo[1,3]dioxol-5-yl-ethylcarbamoyl)-4-hydroxy-phenoxy]-3,5-dibromo-phenyl}-acetic acid | 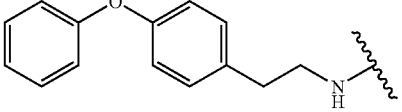 | 593.93 |
| 29 | (3,5-Dibromo-4-{4-hydroxy-3-[2-(4-phenoxy-phenyl)-ethylcarbamoyl]-phenoxy}-phenyl)-acetic acid | 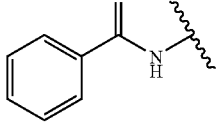 | 641.98 |
| 30 | (R)-{3,5-Dibromo-4-[4-hydroxy-3-(1-phenyl-ethylcarbamoyl)-phenoxy]-phenyl}-acetic acid |  | 550.06 |

-continued

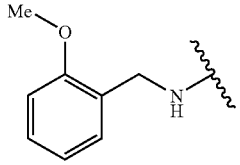

| Example | Name | R | [M + H]+ |
|---|---|---|---|
| 31 | {3,5-Dibromo-4-[4-hydroxy-3-(2-methoxy-benzylcarbamoyl)-phenoxy]-phenyl}-acetic acid | 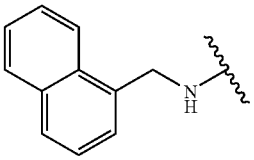 | 565.94 |
| 32 | (3,5-Dibromo-4-{4-hydroxy-3-[(naphthalen-1-ylmethyl)-carbamoyl]-phenoxy}-phenyl)-acetic acid | 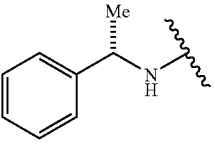 | 585.98 |
| 33 | (S)-{3,5-Dibromo-4-[4-hydroxy-3-(1-phenyl-ethylcarbamoyl)-phenoxy]-phenyl 1-acetic acid | 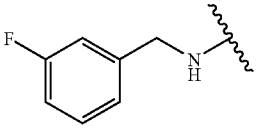 | 549.95 |
| 34 | {3,5-Dibromo-4-[3-(3-fluoro-benzylcarbamoyl)-4-hydroxy-phenoxy]-phenyl}-acetic acid | 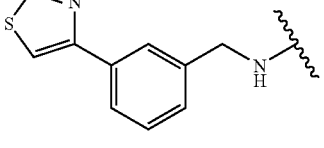 | 553.93 |
| 35 | {3,5-Dibromo-4-[4-hydroxy-3-(4-[1,2,3]thiadiazol-4-yl-benzylcarbamoyl)-phenoxy]-phenyl}-acetic acid | 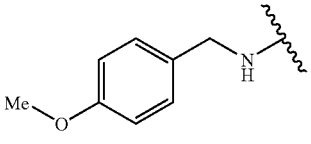 | 619.92 |
| 36 | {3,5-Dibromo-4-[4-hydroxy-3-(4-methoxy-benzylcarbamoyl)-phenoxy]-phenyl}-acetic acid | 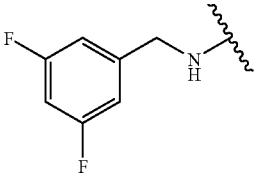 | 565.94 |
| 37 | {3,5-Dibromo-4-[3-(3,5-difluoro-benzylcarbamoyl)-4-hydroxy-phenoxy]-phenyl}-acetic acid | 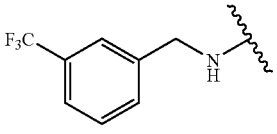 | 571.93 |
| 38 | {3,5-Dibromo-4-[4-hydroxy-3-(3-trifluoromethyl-benzylcarbamoyl)-phenoxy]-phenyl}-acetic acid |  | 603.89 |

-continued

| Example | Name | R | [M + H]+ |
|---|---|---|---|
| 39 | {3,5-Dibromo-4-[3-(3,4-difluoro-benzylcarbamoyl)-4-hydroxy-phenoxy]-phenyl}1-acetic acid | 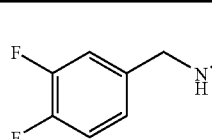 | 571.92 |
| 40 | (3,5-Dibromo-4-{3-[2-(3,4-dimethoxy-phenyl)-ethylcarbamoyl]-4-hydroxy-phenoxy}-phenyl)-acetic acid | 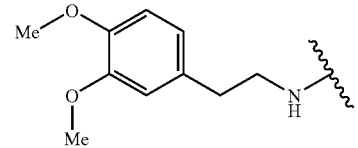 | 549.96 |
| 41 | {3,5-Dibromo-4-[4-hydroxy-3-(4-trifluoromethyl-benzylcarbamoyl)-phenoxy]-phenyl}-acetic acid | 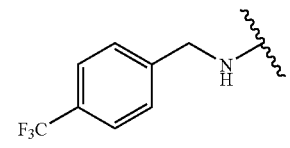 | 603.89 |
| 42 | (3,5-Dibromo-4-{3-[(furan-2-ylmethyl)-carbamoyl]-4-hydroxy-phenoxy}-phenyl)-acetic acid | 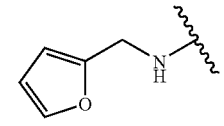 | 525.95 |
| 43 | {3,5-Dibromo-4-[4-hydroxy-3-(4-sulfamoyl-benzylcarbamoyl)-phenoxy]-phenyl}-acetic acid | 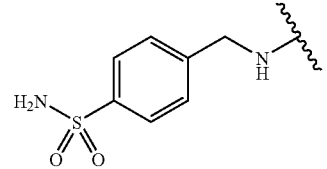 | 614.90 |
| 44 | {3,5-Dibromo-4-[3-(2,3-dimethyl-benzylcarbamoyl)-4-hydroxy-phenoxy]-phenyl}-acetic acid | 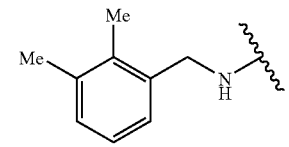 | 563.94 |
| 45 | {3,5-Dibromo-4-[3-(3,5-dimethyl-benzylcarbamoyl)-4-hydroxy-phenoxy]-phenyl}-acetic acid | 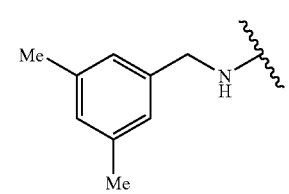 | 563.96 |
| 46 | {3,5-Dibromo-4-[4-hydroxy-3-(3-methoxy-benzylcarbamoyl)-phenoxy]-phenyl}-acetic acid | 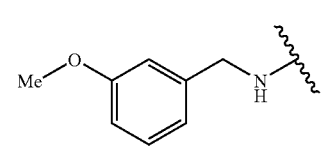 | 565.94 |

-continued

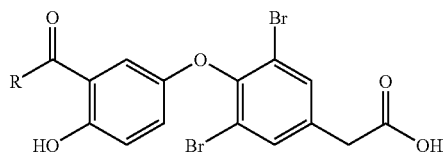

| Example | Name | R | [M + H]+ |
|---|---|---|---|
| 47 | {3,5-Dibromo-4-[4-hydroxy-3-(2-methyl-benzylcarbamoyl)-phenoxy]-phenyl}-acetic acid | 2-methylbenzyl-NH- | 549.96 |
| 48 | {3,5-Dibromo-4-[4-hydroxy-3-(2-trifluoromethyl-benzylcarbamoyl)-phenoxy]-phenyl}-acetic acid | 2-(trifluoromethyl)benzyl-NH- | 603.92 |
| 49 | {4-[3-(Benzyl-methyl-carbamoyl)-4-hydroxy-phenoxy]-3,5-dibromo-phenyl}-acetic acid | benzyl-N(Me)- | 550.05 |
| 50 | {3,5-Dibromo-4-[4-hydroxy-3-(4-methyl-benzylcarbamoyl)-phenoxy]-phenyl}-acetic acid | 4-methylbenzyl-NH- | 549.94 |
| 51 | {3,5-Dibromo-4-[3-(3-chloro-4-fluoro-benzylcarbamoyl)-4-hydroxy-phenoxy]-phenyl}-acetic acid | 3-chloro-4-fluorobenzyl-NH- | 587.89 |
| 52 | {3,5-Dibromo-4-[3-(2-fluoro-benzylcarbamoyl)-4-hydroxy-phenoxy]-phenyl}-acetic acid | 2-fluorobenzyl-NH- | 553.96 |
| 53 | (3,5-Dibromo-4-{3-[2-(2-fluoro-phenyl)-ethylcarbamoyl]-4-hydroxy-phenoxy}-phenyl)-acetic acid | 2-(2-fluorophenyl)ethyl-NH- | 567.94 |
| 54 | {3,5-Dibromo-4-[3-(2,2-diphenyl-ethylcarbamoyl)-4-hydroxy-phenoxy]-phenyl}-acetic acid | 2,2-diphenylethyl-NH- | 625.95 |

-continued

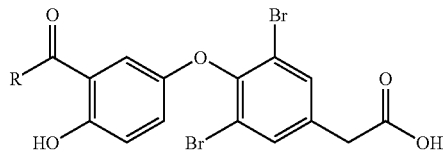

| Example | Name | R | [M + H]⁺ |
|---|---|---|---|
| 55 | {3,5-Dibromo-4-[3-(2-chloro-4-fluoro-benzylcarbamoyl)-4-hydroxy-phenoxy]-phenyl}-acetic acid | 2-Cl, 4-F benzyl-NH- | 587.87 |
| 56 | {3,5-Dibromo-4-[3-(2-chloro-6-fluoro-benzylcarbamoyl)-4-hydroxy-phenoxy]-phenyl}-acetic acid | 2-Cl, 6-F benzyl-NH- | 587.87 |
| 57 | {3,5-Dibromo-4-[3-(2,5-difluoro-benzylcarbamoyl)-4-hydroxy-phenoxy]-phenyl}-acetic acid | 2,5-diF benzyl-NH- | 571.92 |
| 58 | {3,5-Dibromo-4-[3-(2,4-difluoro-benzylcarbamoyl)-4-hydroxy-phenoxy]-phenyl}-acetic acid | 2,4-diF benzyl-NH- | 571.94 |
| 59 | (3,5-Dibromo-4-{4-hydroxy-3-[2-(4-nitro-phenyl)-ethylcarbamoyl]-phenoxy}-phenyl)-acetic acid | 4-NO₂ phenethyl-NH- | 594.92 |
| 60 | (3,5-Dibromo-4-{3-[2-(4-fluoro-phenyl)-ethylcarbamoyl]-4-hydroxy-phenoxy}-phenyl)-acetic acid | 4-F phenethyl-NH- | 567.94 |
| 61 | {3,5-Dibromo-4-[3-(3,4-dimethyl-benzylcarbamoyl)-4-hydroxy-phenoxy]-phenyl}-acetic acid | 3,4-diMe benzyl-NH- | 563.98 |
| 62 | {3,5-Dibromo-4-[3-(4-fluoro-benzylcarbamoyl)-4-hydroxy-phenoxy]-phenyl}-acetic acid | 4-F benzyl-NH- | 553.93 |

Example 63

{3,5-Dibromo-4-[4-hydroxy-3-(phenethylamino-methyl)-phenoxy]-phenyl}-acetic Acid

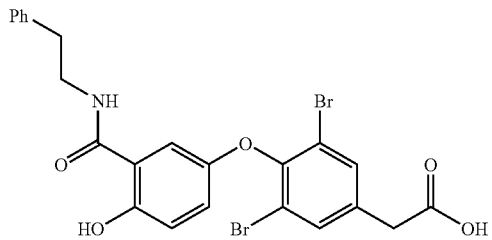

63A

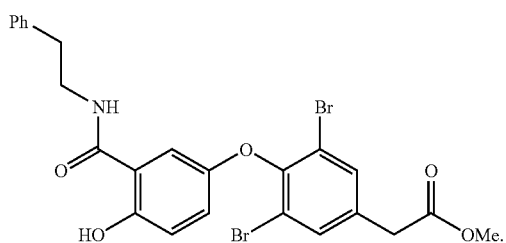

A mixture of compound 1D (36.3 mg, 0.08 mmol), trimethylorthoformate (78 mg, 0.79 mmol) and phenethylamine (78.8 mg, 0.65 mmol) in 1 mL of CH2Cl2 was stirred at room temperature overnight, then diluted with 2 mL of CH2Cl2 and treated with sodium triacetoxyborohydride (209 mg, 1 mmol) followed by acetic acid (42 mg, 0.7 mmol). The reaction was stirred at room temperature for 4 hours, then treated with water and stirred for 30 minutes. Solid sodium carbonate was added to adjust the reaction mixture to pH 7. More water (2 mL) was added and the product extracted with CH2Cl2. The organic extract was washed with brine and concentrated in vacuo. Flash chromatography (silica gel, 1:10:500 2M NH3 in MeOH/MeOH/CH2Cl2) provided 34.6 mg (79%) of product amine, Compound 63A (satisfactory 1H and 13C NMR were obtained).

Example 63

Compound 63A (28.2 mg, 0.051 mmol) was treated with a mixture of 0.7 mL of methanol and 0.2 mL of 1N aqueous sodium hydroxide and the resulting mixture was stirred at room temperature for 2 hours. The reaction mixture was then chromatographed on 20 mL of HP-20 resin eluted first with water, then acetone:water mixtures initially 10% acetone until at 50% acetone, the desired product eluted. Pooling of product containing fractions and evaporation of solvents yielded 23.4 mg (82%) of Example 63 (HPLC purity 98.3%, satisfactory MS (536.2, [M+H]$^+$) and 1H and 13C NMR were obtained).

Example 64

{3,5-Dibromo-4-[4-hydroxy-3-(3-phenyl-propionylamino)-phenoxy]-phenyl}-acetic Acid

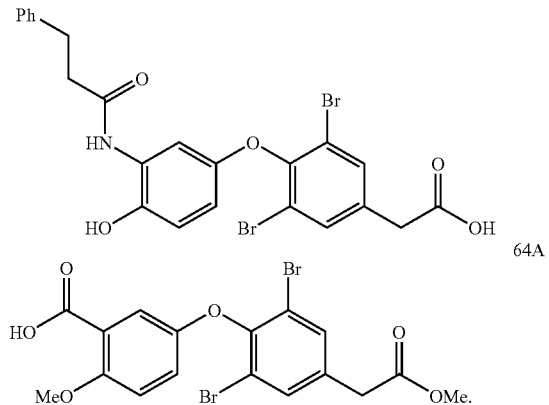

Compound 1C (458 mg, 1 mmol) was dissolved in 6 mL of 2:1 THF/water. The reaction mixture was cooled with an ice-bath and treated with 1.3 mL of 1M aqueous sulfamic acid solution followed by 1.4 mL of 1M aqueous sodium chlorite solution. After 40 minutes the reaction was diluted with 10 mL of water and the product extracted with CH2Cl2. The organic extract was washed with brine, dried over Na2SO4 and concentrated in vacuo to provide 0.45 g of carboxylic acid product, Compound 64A which was used as such in the next reaction (satisfactory 1H and 13C NMR were obtained).

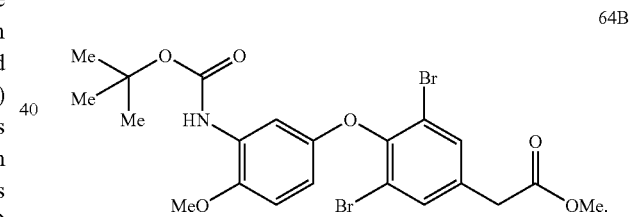

Diphenylphosphoryl azide (0.056 mL, 0.26 mmol) was added to a mixture of Compound 64A (115 mg, 0.25 mmol), triethylamine (0.04 mL, 0.28 mmol), t-butanol (200 mg, 2.7 mmol) and 100 mg of 4 A molecular sieves in 1 mL of dioxane. The reaction mixture was heated to reflux for 24 hours, then concentrated in vacuo and flash chromatographed (silica gel, ethyl acetate/hexane) to provide 58.3 mg (43%) of t-butyl carbamate product, Compound 64B (satisfactory 1H and 13C NMR were obtained).

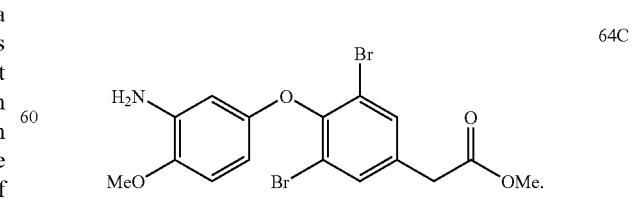

Compound 64B (17 mg, 0.031 mmol) was dissolved in 1 mL of CH2Cl2. Trifluoroacetic acid (0.25 mL) was added and the reaction kept at room temperature for 4 hours. Solvents were removed in vacuo and the product extracted into ethyl acetate. The organic extract was washed with saturated NaHCO3 solution and brine, dried over Na2SO4 and concentrated in vacuo to provide 13 mg of amine product, Compound 64C (satisfactory 1H and 13C NMR were obtained) which was used in the next reaction without further purification.

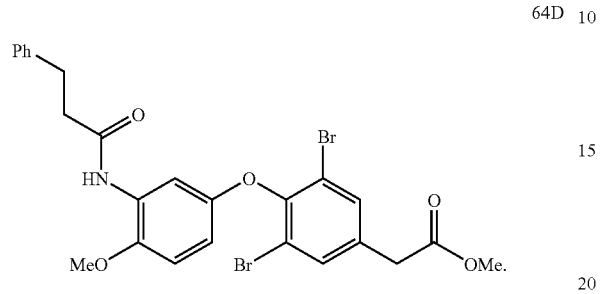

64D

To a mixture containing Compound 64C (13 mg, 0.029 mmol), hydrocinnamic acid (4.8 mg, 0.03 mmol), and HOAT (4.8 mg, 0.035 mmol) in 0.6 mL of 5:1 CH2Cl2/DMF at room temperature was added WSC (6.7 mg, 0.035 mmol). The reaction was stirred at room temperature overnight, then diluted with 20 mL of CH2Cl2. The organic extract was washed with water, saturated NaHCO3 solution and brine, dried over Na2SO4 and concentrated in vacuo. Flash chromatography (silica gel, ethyl acetate/toluene) provided 10.9 mg (62%) of amide product, Compound 64D (satisfactory 1H and 13C NMR were obtained).

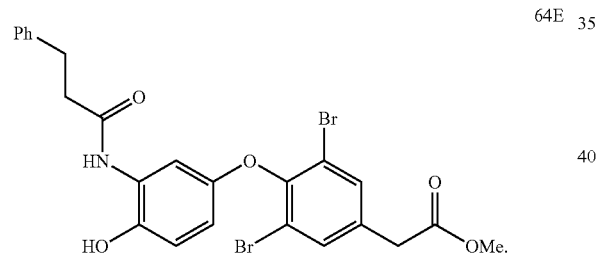

64E

Compound 64D (10.9 mg, 0.019 mmol) dissolved in 0.2 mL of CH2Cl2 was added dropwise to a solution of 0.1 mL of boron tribromide in 0.5 mL of CH2Cl2 at −49° C. under argon. The reaction mixture was stirred at room temperature for 2 hours, then poured into a rapidly stirred mixture of ethyl acetate and saturated NaHCO3 solution. The organic extract was rinsed with brine, dried over Na2SO4 and concentrated in vacuo to yield 8.3 mg (78%) of desired product, Compound 64E (satisfactory 1H NMR was obtained), which was used in the next reaction without further purification.

Example 64

Compound 64E (8.3 mg, 0.015 mmol) was dissolved in a mixture of 0.2 mL of methanol and 0.2 mL of 1N aqueous sodium hydroxide solution. The reaction was stirred at room temperature for 4 hours, then concentrated in vacuo to remove most of the methanol. Water was added to the concentrated residue, which was then acidified with 1N aqueous hydrochloric acid and extracted with ethyl acetate. The organic extract was washed with brine, dried over Na2SO4 and concentrated in vacuo. Lyophillization from dioxane afforded 4.6 mg (57%) of Example 64 (HPLC purity 89.6%, satisfactory MS (550.0, [M+H]$^+$) and 1H and 13C NMR were obtained).

Example 65

{3,5-Dibromo-4-[4-hydroxy-3-(4-trifluoromethyl-phenoxy)-phenoxy]-phenyl}-acetic Acid

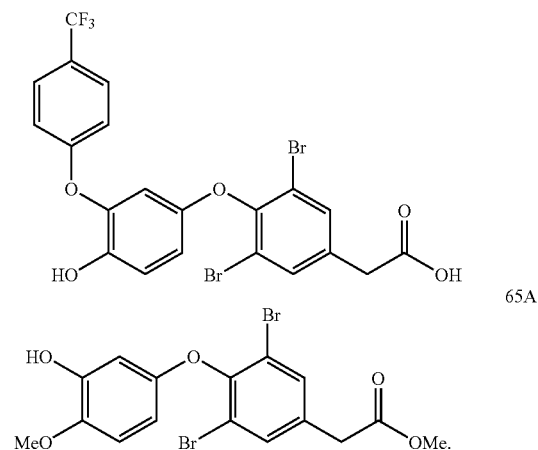

65A m-Chloroperbenzoic acid (172 mg, 1 mmol) dissolved in 3 mL of chloroform was added dropwise to Compound 1C (387 mg, 0.84 mmol) dissolved in 5 mL of chloroform. The reaction was stirred at room temperature under argon overnight. The reaction was next diluted with ether and the organic extract washed with 5% aqueous NaHSO3, saturated NaHCO3 and brine, the dried over Na2SO4 and concentrated in vacuo to give the intermediate formate ester Baeyer-Villager reaction product. The formate product was dissolved in 10 mL of methanol and treated with 5 mL of 5N hydrochloric acid in dioxane. The reaction mixture was stirred for 3 hours at room temperature, the concentrated in vacuo and evaporated with several portions of toluene. After removal of solvents in vacuo, 332 mg (89%) of Compound 65A was obtained as a solid product (satisfactory 1H and 13C NMR were obtained).

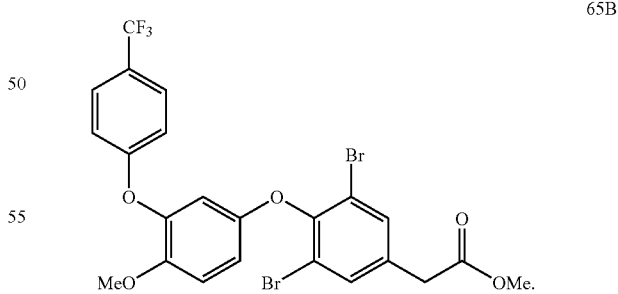

65B

A mixture containing Compound 65A (30 mg, 0.067 mmol), p-trifluoromethylphenyl boronic acid (38 mg, 0.201 mmol), copper(II) acetate (13 mg, 0.07 mmol) and 120 mg of crushed 4 Å molecular sieves in 0.67 mL of CH2Cl2 was shaken for 10 minutes, then treated with pyridine (0.033 mL, 0.41 mmol) and triethylamine (0.057 mL, 0.41 mmol). After 3 days the reaction mixture was diluted with ethyl acetate, filtered over Celite and flash chromatographed (silica gel, 7.5% ethyl acetate/hexane) to afford 39.5 mg (52%) diaryl ether coupling product, Compound 65B (satisfactory 1H and 13C NMR were obtained).

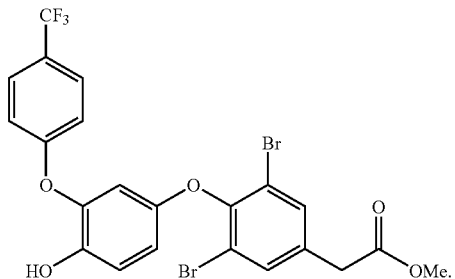

65C

A solution of boron tribromide in CH2Cl2 (2 mL of 1M solution) was cooled to −45° C. under nitrogen. Compound 65B (21 mg, 0.035 mmol) dissolved in 0.5 mL of CH2Cl2 was added dropwise to the BBr3 solution, and the reaction was allowed to warm from −45° C. to 0° C. over 4 hours, then diluted with more CH2Cl2 and poured into a mixture of ethyl acetate and saturated aqueous NaHCO3. The ethyl acetate extract was rinsed with more saturated aqueous NaHCO3, then brine and concentrated in vacuo with several portions of methanol to provide 20 mg of Compound 65C (satisfactory 1H and 13C NMR were obtained), which was used in the next step without further purification.

Example 65

Compound 65C (19.5 mg, 0.0338 mmol) was dissolved in a mixture of 0.4 ML of methanol and 0.3 mL of 1N aqueous sodium hydroxide solution. The reaction was stirred at room temperature for 4 hours, then concentrated in vacuo to remove most of the methanol. Water was added to the concentrated residue, which was then acidified with 1N aqueous hydrochloric acid and extracted with ethyl acetate. The organic extract was washed with brine, dried over Na2SO4 and concentrated in vacuo with toluene to yield 13 mg (68%) of Example 65 obtained as a tan colored solid (HPLC purity 88.3%, satisfactory MS (558.7, [M−H]$^-$) and 1H and 13C NMR were obtained).

Examples 66 to 98

Examples 66 to 98 were prepared by following procedures similar to those described for Example 65.

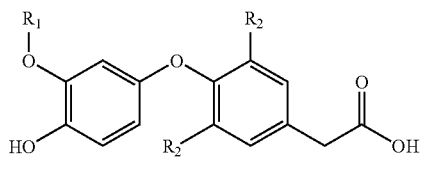

| Example | Name | R1 | R2 | [M − H]$^-$ |
|---|---|---|---|---|
| 66 | [3,5-Dichloro-4-(4-hydroxy-3-phenoxy-phenoxy)-phenyl]-acetic acid | phenyl | Cl | 403.2 |
| 67 | {3,5-Dichloro-4-[4-hydroxy-3-(4-hydroxy-phenoxy)-phenoxy]-phenyl}-acetic acid | 4-hydroxyphenyl | Cl | 419.0 |
| 68 | {3,5-Dibromo-4-[3-(3,5-dichloro-phenoxy)-4-hydroxy-phenoxy]-phenyl}-acetic acid | 3,5-dichlorophenyl | Br | 558.7 |
| 69 | [3,5-Dibromo-4-(4-hydroxy-3-p-tolyloxy-phenoxy)-phenyl]-acetic acid | 4-methylphenyl | Br | 504.7 |
| 70 | {3,5-Dibromo-4-[3-(4-chloro-phenoxy)-4-hydroxy-phenoxy]-phenyl}-acetic acid | 4-chlorophenyl | Br | 524.7 |
| 71 | {3,5-Dibromo-4-[3-(4-fluoro-phenoxy)-4-hydroxy-phenoxy]-phenyl}-acetic acid | 4-fluorophenyl | Br | 509 |

-continued

| Example | Name | R1 | R2 | [M − H]⁻ |
|---|---|---|---|---|
| 72 | [3,5-Dibromo-4-(4-hydroxy-3-phenoxy-phenoxy)-phenyl]-acetic acid | 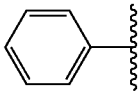 | Br | 491 |
| 73 | {3,5-Dibromo-4-[4-hydroxy-3-(naphthalen-1-yloxy)-phenoxy]-phenyl}-acetic acid | 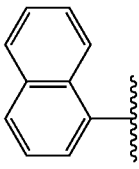 | Br | 541 |
| 74 | {3,5-Dibromo-4-[4-hydroxy-3-(2-trifluoromethyl-phenoxy)-phenoxy]-phenyl}-acetic acid | 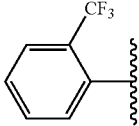 | Br | 559 |
| 75 | {4-[3-(Biphenyl-4-yloxy)-4-hydroxy-phenoxy]-3,5-dibromo-phenyl}-acetic acid | 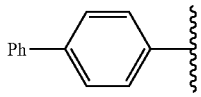 | Br | 569.0 |
| 76 | {4-[3-(Biphenyl-3-yloxy)-4-hydroxy-phenoxy]-3,5-dibromo-phenyl}-acetic acid | 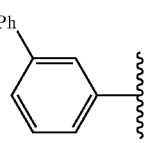 | Br | 569.0 |
| 77 | {3,5-Dibromo-4-[4-hydroxy-3-(4-isopropyl-phenoxy)-phenoxy]-phenyl}-acetic acid | 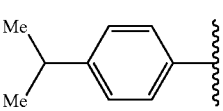 | Br | 535.0 |
| 78 | {3,5-Dibromo-4-[4-hydroxy-3-(4-methyl-3-nitro-phenoxy)-phenoxy]-phenyl}-acetic acid | 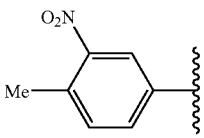 | Br | 550 |
| 79 | {3,5-Dibromo-4-[4-hydroxy-3-(naphthalen-2-yloxy)-phenoxy]-phenyl}-acetic acid | 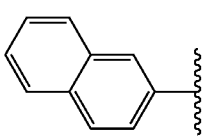 | Br | 541 |
| 80 | {3,5-Dibromo-4-[4-hydroxy-3-(2-hydroxy-phenoxy)-phenoxy]-phenyl}-acetic acid | 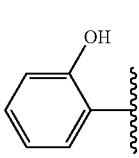 | Br | 507 |
| 81 | {3,5-Dibromo-4-[4-hydroxy-3-(4-hydroxy-phenoxy)-phenoxy]-phenyl}-acetic acid | 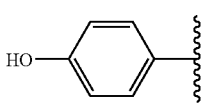 | Br | 507 |

-continued

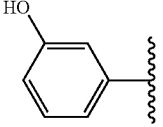

| Example | Name | R1 | R2 | [M − H]⁻ |
|---|---|---|---|---|
| 82 | {3,5-Dibromo-4-[4-hydroxy-3-(3-hydroxy-phenoxy)-phenoxy]-phenyl}-acetic acid | 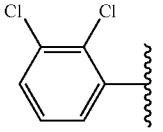 | Br | 507 |
| 83 | {3,5-Dibromo-4-[3-(2,3-dichloro-phenoxy)-4-hydroxy-phenoxy]-phenyl}-acetic acid | 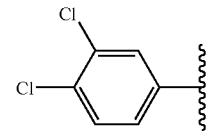 | Br | 560.8 |
| 84 | {3,5-Dibromo-4-[3-(3,4-dichloro-phenoxy)-4-hydroxy-phenoxy]-phenyl}-acetic acid | 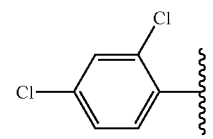 | Br | 560.9 |
| 85 | {3,5-Dibromo-4-[3-(2,4-dichloro-phenoxy)-4-hydroxy-phenoxy]-phenyl}-acetic acid | 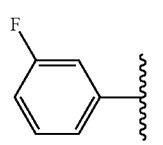 | Br | 560.8 |
| 86 | {3,5-Dibromo-4-[3-(3-fluoro-phenoxy)-4-hydroxy-phenoxy]-phenyl}-acetic acid | 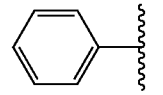 | Br | 509 |
| 87 | [3-Bromo-4-(4-hydroxy-3-phenoxy-phenoxy)-5-methyl-phenyl]-acetic acid | 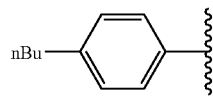 | Br, Me | 427.4 |
| 88 | {3,5-Dibromo-4-[3-(4-butyl-phenoxy)-4-hydroxy-phenoxy]-phenyl}-acetic acid | 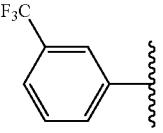 | Br | 547 |
| 89 | {3,5-Dibromo-4-[4-hydroxy-3-(3-trifluoromethyl-phenoxy)-phenoxy]-phenyl}-acetic acid | 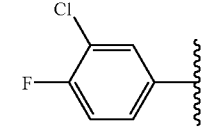 | Br | 559 |
| 90 | {3,5-Dibromo-4-[3-(3-chloro-4-fluoro-phenoxy)-4-hydroxy-phenoxy]-phenyl}-acetic acid | 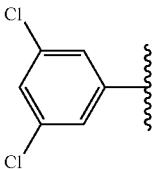 | Br | 543 |
| 91 | {3,5-Dichloro-4-[3-(3,5-dichloro-phenoxy)-4-hydroxy-phenoxy]-phenyl}-acetic acid |  | Cl | 471 |

-continued

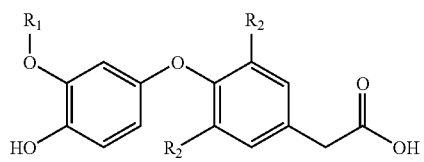

| Example | Name | R1 | R2 | [M − H]⁻ |
|---|---|---|---|---|
| 92 | {3,5-Dibromo-4-[4-hydroxy-3-(4-trifluoromethoxy-phenoxy)-phenoxy]-phenyl}-acetic acid | CF₃O–C₆H₄– | Br | 575 |
| 93 | {3,5-Dibromo-4-[3-(4-fluoro-phenoxy)-4-hydroxy-phenoxy]-phenyl}-acetic acid | F–C₆H₄– | Br | 509 |
| 94 | [3,5-Dichloro-4-(4-hydroxy-3-p-tolyloxy-phenoxy)-phenyl]-acetic acid | Me–C₆H₄– | Cl | Not available |
| 95 | {3,5-Dichloro-4-[4-hydroxy-3-(4-trifluoromethyl-phenoxy)-phenoxy]-phenyl}-acetic acid | F₃C–C₆H₄– | Cl | 470.9 |
| 96 | {3,5-Dichloro-4-[3-(4-fluoro-phenoxy)-4-hydroxy-phenoxy]-phenyl}-acetic acid | F–C₆H₄– | Cl | 421 |
| 97 | {3,5-Dichloro-4-[4-hydroxy-3-(2-trifluoromethyl-phenoxy)-phenoxy]-phenyl}-acetic acid | 2-CF₃–C₆H₄– | Cl | 471.0 |
| 98 | {3,5-Dibromo-4-[4-hydroxy-3-(thiophen-3-yloxy)-phenoxy]-phenyl}-acetic acid | thiophen-3-yl | Br | 497 |

Example 99

[3,5-Dichloro-4-(6-hydroxy-biphenyl-3-yloxy)-phenyl]-acetic Acid

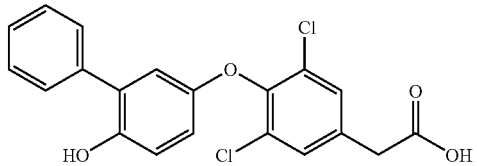

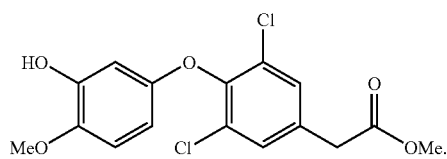
99A

Compound 99A was prepared from aldehyde intermediate 2E by following the procedure described for intermediate 65A (satisfactory 1H and 13C NMR were obtained).

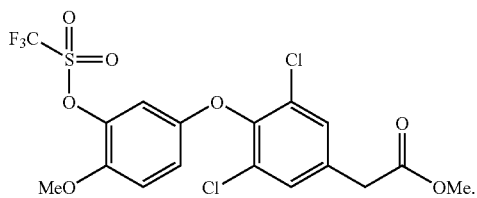
99B

Triflic anhydride (0.094 mL, 0.56 mmol) was added dropwise to a solution containing compound 99A (0.2 g, 0.56 mmol) and triethylamine (0.078 mL, 0.56 mmol) in dry methylene chloride (7 mL) cooled to −40° C. under argon. The reaction was stirred for 1 h at −40° C. to −10° C., then water was added and the product extracted with additional methylene chloride. Work-up and flash chromatography (silica gel, 1/5 EtOAc/hexanes) yielded 0.22 g (81%) of Compound 99B (satisfactory 1H and 13C NMR were obtained).

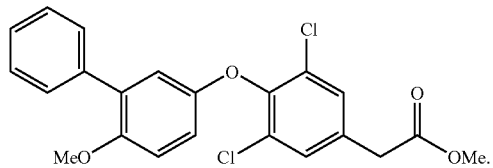
99C

A mixture containing Compound 99B (47.7 mg, 0.0975 mmol), phenylboronic acid (23.8 mg, 0.195 mmol), potassium carbonate (20.3 mg, 0.147 mmol) and palladium tetrakis-triphenylphosphine (11 mg) in 0.8 mL of degassed toluene was heated at 85 to 95° C. for 2 h. Flash chromatography (silica gel, 1/9 EtOAc/hexanes) provided 30.7 mg (75%) of Compound 99C (satisfactory 1H and 13C NMR were obtained).

Example 99

Example 99 was obtained in two steps from Compound 99C by (1) demethylation of the phenolic methyl ether group (following the procedure described for the conversion of Compound 65B to Compound 65C), followed by (2) saponification of the methyl ester group (following the procedure described for the conversion of Compound 65C to Example 65). Compound 99C exhibited satisfactory MS (387.3, [M−H]⁻) and 1H and 13C NMR spectra.

Example 100

[3,5-Dichloro-4-(6-hydroxy-4'-trifluoromethyl-biphenyl-3-yloxy)-phenyl]-acetic Acid

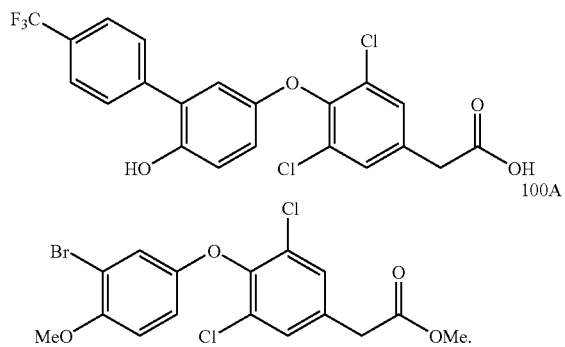
100A

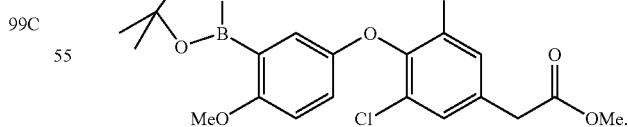

Bromine (1.9 g, 12.4 mmol) was added dropwise to a rapidly stirring solution of Compound 2D (1.7 g, 5.0 mmol) in 20 mL glacial acetic acid. After 1 h, the reaction was diluted with ethyl acetate, washed with 10% aqueous NaHSO₃, water, saturated aqueous sodium bicarbonate and brine. The organic layer was dried over anhydrous magnesium sulfate, filtered and evaporated to dryness yielding 2.17 g (>99%) crude bromide Compound 100A of suitable purity for the next step. A 1H NMR obtained was consistent with the proposed structure.

100B

Anhydrous potassium acetate (0.74 g, 7.5 mmol), [1,1'-bis(diphenylphosphino)ferrocene]dichloropalladium(II) methylene chloride complex (0.4 g, 0.5 mmol), and bis(pinacolato)diboron (1.9 g, 7.5 mmol) were placed under argon and treated with a degassed solution consisting of Compound 100A (1.1 g, 2.5 mmol) and dimethylsulfoxide (15 mL). The mixture was stirred at 80° C. for 4 h, cooled to room temperature, diluted with EtOAc and washed with water and brine, dried over magnesium sulfate, filtered and evaporated in vacuo. Compound 100B (0.93 g, 80%) was isolated by silica gel chromatography (1/9 to 3/7, EtOAc/hexanes). It exhibited 1H and 13C NMR spectra consistent with the assigned structure.

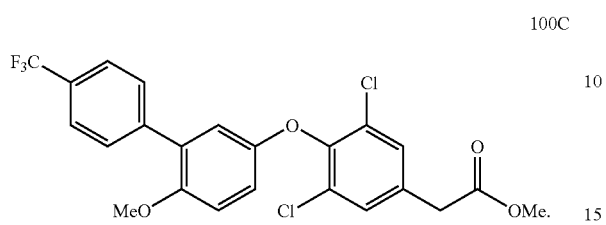

100C

4-Trifluorobromobenzene (81 mg, 0.36 mmol), [1,1'-bis(diphenylphosphino)ferrocene]dichloropalladium(II) methylene chloride complex (10 mg, 0.013 mmol), and potassium carbonate (26 mg, 0.19 mmol) were placed under argon and treated with a degassed solution of Compound 100B (30 mg, 0.064 mmol) in dimethylsulfoxide (0.4 mL). The reaction was heated to 80° C. for 1.5 h, cooled to room temperature, diluted with EtOAc, washed with water and brine, dried over magnesium sulfate, filtered and evaporated in vacuo. Compound 100C (18 mg, 58%) was isolated by preparative thin layer silica gel chromatography (4/6, EtOAc/hexanes). It exhibited 1H and 13C NMR spectra consistent with the assigned structure.

Example 100

Example 100 was obtained in two steps from Compound 100C by (1) demethylation of the phenolic methyl ether group (following the procedure described for the conversion of Compound 65B to Compound 65C), followed by (2)saponification of the methyl ester group (following the procedure described for the conversion of Compound 65C to Example 65). Satisfactory MS (454.9, [M−H]⁻) and 1H and 13C NMR were obtained.

Example 101

[3,5-Dichloro-4-(3'-ethyl-6-hydroxy-biphenyl-3-yloxy)-phenyl]-acetic Acid

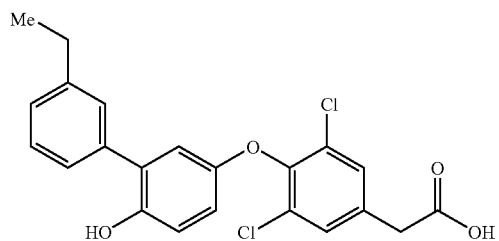

Example 101 was prepared in a manner analogous to that described for Example 100, except that the palladium(II) catalyst employed for the coupling reaction between 2-bromopyridine with Compound 100B was tetrakis(triphenylphosphine)palladium(0). Satisfactory MS (415, [M−H]⁻) and 1H and 13C NMR were obtained.

Examples 102 to 133

Examples 102 to 133, wherein an aryl group is located at the R4 position (R8=aryl), were prepared by following procedures similar to those described above for Examples 99 to 101.

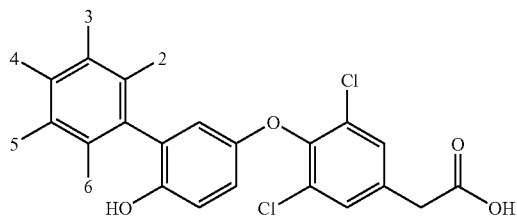

| Example | Name | Substitution | [M − H]⁻ |
|---|---|---|---|
| 102 | [3,5-Dichloro-4-(6,3'-dihydroxy-biphenyl-3-yloxy)-phenyl]-acetic acid | 3-OH | 403.0 |
| 103 | [4-(3'-Carbamoyl-6-hydroxy-biphenyl-3-yloxy)-3,5-dichloro-phenyl]-acetic acid | 3-CONH2 | 429.9 |
| 104 | [4-(4'-Carbamoyl-6-hydroxy-biphenyl-3-yloxy)-3,5-dichloro-phenyl]-acetic acid | 4-CONH2 | 430.0 |
| 105 | [3,5-Dichloro-4-(6-hydroxy-2'-hydroxymethyl-biphenyl-3-yloxy)-phenyl]-acetic acid | 2-CH2OH | 298.9 [M − H3O]⁻ |
| 106 | [3,5-Dichloro-4-(6-hydroxy-4'-methyl-biphenyl-3-yloxy)-phenyl]-acetic acid | 4-Me | 401 |
| 107 | [3,5-Dichloro-4-(6-hydroxy-3'-methyl-biphenyl-3-yloxy)-phenyl]-acetic acid | 3-Me | 401 |
| 108 | [3,5-Dichloro-4-(6-hydroxy-2'-trifluoromethyl-biphenyl-3-yloxy)-phenyl]-acetic acid | 2-CF3 | 455.0 |
| 109 | [3,5-Dichloro-4-(6,4-dihydroxy-biphenyl-3-yloxy)-phenyl]-acetic acid | 4-OH | 403.0 |

-continued

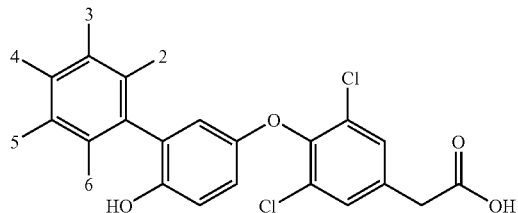

| Example | Name | Substitution | [M − H]⁻ |
|---|---|---|---|
| 110 | [3,5-Dichloro-4-(6-hydroxy-3'-trifluoromethyl-biphenyl-3-yloxy)-phenyl]-acetic acid | 3-CF3 | 454.9 |
| 111 | [3,5-Dichloro-4-(4-fluoro-6-hydroxy-biphenyl-3-yloxy)-phenyl]-acetic acid | 4-F | 405.0 |
| 112 | [3,5-Dichloro-4-(6-hydroxy-[1,1';4',1'']terphenyl-3-yloxy)-phenyl]-acetic acid | 4-Ph | 463 |
| 113 | [3,5-Dichloro-4-(6-hydroxy-[1,1';3',1'']terphenyl-3-yloxy)-phenyl]-acetic acid | 3-Ph | 463 |
| 114 | [3,5-Dichloro-4-(6,2'-dihydroxy-biphenyl-3-yloxy)-phenyl]-acetic acid | 2-OH | 403 |
| 115 | [3,5-Dichloro-4-(6-hydroxy-2',4'-dimethyl-biphenyl-3-yloxy)-phenyl]-acetic acid | 2,4-diMe | 415 |
| 116 | [3,5-Dichloro-4-(6-hydroxy-2',3'-dimethyl-biphenyl-3-yloxy)-phenyl]-acetic acid | 2,3-diMe | 415 |
| 117 | [3,5-Dichloro-4-(6-hydroxy-3',5'-dimethyl-biphenyl-3-yloxy)-phenyl]-acetic acid | 3,5-diMe | 415 |
| 118 | [3,5-Dichloro-4-(6-hydroxy-3',4'-dimethyl-biphenyl-3-yloxy)-phenyl]-acetic acid | 3,4-diMe | 415 |
| 119 | [3,5-Dichloro-4-(6-hydroxy-2',5'-dimethyl-biphenyl-3-yloxy)-phenyl]-acetic acid | 2,5-diMe | 415 |
| 120 | [3,5-Dichloro-4-(3'-chloro-6-hydroxy-biphenyl-3-yloxy)-phenyl]-acetic acid | 3-Cl | 421 |
| 121 | [3,5-Dichloro-4-(3'-fluoro-6-hydroxy-biphenyl-3-yloxy)-phenyl]-acetic acid | 3-F | 405 |
| 122 | [4-(3-Acetyl-6-hydroxy-biphenyl-3-yloxy)-3,5-dichloro-phenyl]-acetic acid | 3-COMe | 429 |
| 123 | [3,5-Dichloro-4-(6-hydroxy-4'-phenoxy-biphenyl-3-yloxy)-phenyl]-acetic acid | 4-OPh | 479 |
| 124 | [4-(5'-tert-Butyl-6-hydroxy-2-methyl-biphenyl-3-yloxy)-3,5-dichloro-phenyl]-acetic acid | 2-Me, 5-tertBu | 457 |
| 125 | [3,5-Dichloro-4-(6-hydroxy-2',4',5'-trimethyl-biphenyl-3-yloxy)-phenyl]-acetic acid | 2,4,5-triMe | 429 |
| 126 | [3,5-Dichloro-4-(6-hydroxy-3'-propyl-biphenyl-3-yloxy)-phenyl]-acetic acid | 3-nPr | 429 |
| 127 | [3,5-Dichloro-4-(6-hydroxy-3'-isobutyl-biphenyl-3-yloxy)-phenyl]-acetic acid | 3-isoBu | 443 |
| 128 | [3,5-Dichloro-4-(3'-heptyl-6-hydroxy-biphenyl-3-yloxy)-phenyl]-acetic acid | 3-nHeptyl | 485 |
| 129 | [3,5-Dichloro-4-(6-hydroxy-3'-isopropyl-biphenyl-3-yloxy)-phenyl]-acetic acid | 3-isoPr | 429 |
| 130 | [3,5-Dichloro-4-(6-hydroxy-3-methoxy-biphenyl-3-yloxy)-phenyl]-acetic acid | 3-OMe | 417 |
| 131 | [3,5-Dichloro-4-(3'-ethoxy-6-hydroxy-biphenyl-3-yloxy)-phenyl]-acetic acid | 3-OEt | 431 |
| 132 | [3,5-Dichloro-4-(3'-difluoromethoxy-6-hydroxy-biphenyl-3-yloxy)-phenyl]-acetic acid | 3-OCHF2 | 453 |
| 133 | [3,5-Dichloro-4-(6-hydroxy-3-trifluoromethoxy-biphenyl-3-yloxy)-phenyl]-acetic acid | 3-OCF3 | 471 |

Examples 134 to 139

Examples 134 to 139, wherein an aryl group is located at the R4 position (R8=aryl), were also prepared by following procedures similar to those described above for Examples 99 to 101.

| Example | Name | Structure | [M − H]⁻ |
|---|---|---|---|
| 134 | [3,5-Dibromo-4-(6-hydroxy-biphenyl-3-yloxy)-phenyl]-acetic acid | 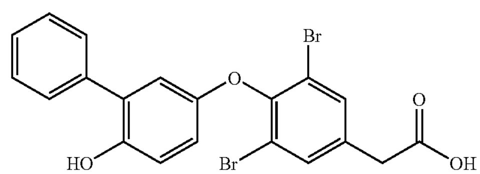 | 476 |
| 135 | [3,5-Dichloro-4-(4-hydroxy-3-naphthalen-1-yl-phenoxy)-phenyl]-acetic acid | 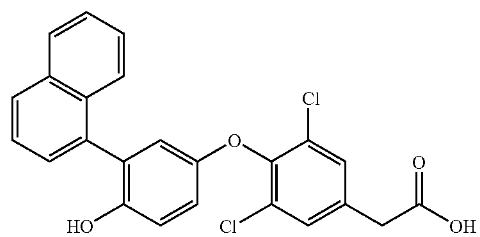 | 437 |
| 136 | {3,5-Dichloro-4-[3-(9H-fluoren-2-yl)-4-hydroxy-phenoxy]-phenyl}-acetic acid | 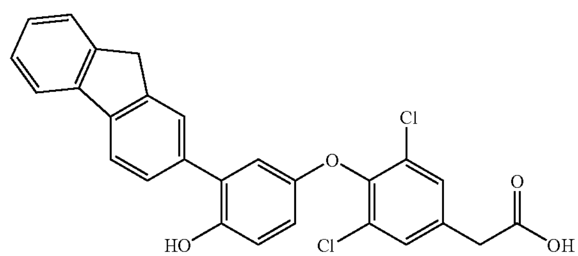 | 475 |
| 137 | 3-[3,5-Dibromo-4-(6-hydroxy-biphenyl-3-yloxy)-phenyl]-propionic acid | 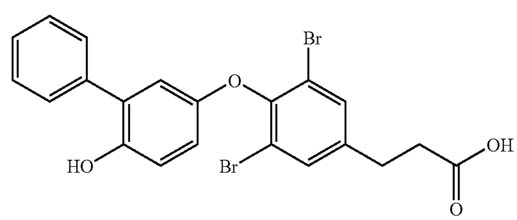 | 490 |
| 138 | 3,5-Dibromo-4-(6-hydroxy-biphenyl-3-yloxy)-benzoic acid | 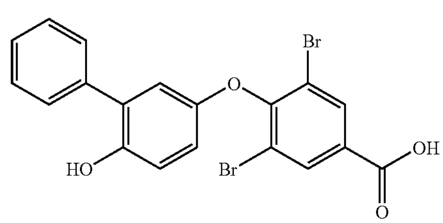 | 462 |
| 139 | 3,5-Dichloro-4-(6-hydroxy-biphenyl-3-yloxy)-benzoic acid | 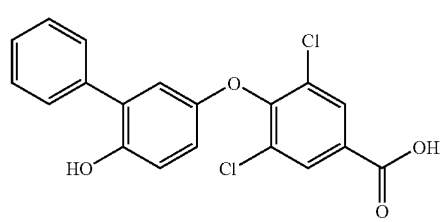 | 373 |

Example 140

[3,5-Dichloro-4-(3-cyclohexyl-4-hydroxy-phenoxy)-phenyl]-acetic Acid

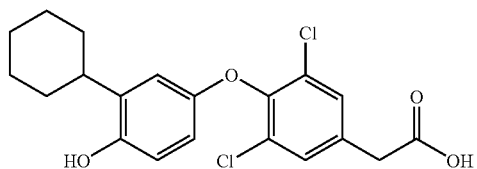

Example 140, wherein a cycloalkyl (specifically, cyclohexyl) group is located at the R4 position (R8=cycloalkyl), was prepared by following procedures similar to those described above for Examples 99 to 101. Satisfactory MS (392.9, [M–H]⁻) and 1H and 13C NMR were obtained.

Examples 141 to 147

Examples 141 to 147, wherein a heteroaryl group is located at the R4 position (R8=heteroaryl), were also prepared by following procedures similar to those described above for Examples 99 to 101.

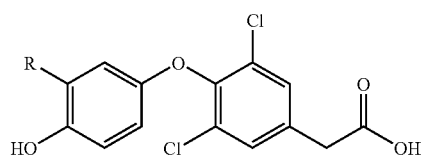

| Example | Name | R | [M – H]⁻ |
|---------|------|---|----------|
| 141 | [3,5-Dichloro-4-(4-hydroxy-3-pyridin-3-yl-phenoxy)-phenyl]-acetic acid | pyridin-3-yl | 387.8 |
| 142 | [3,5-Dichloro-4-(4-hydroxy-3-pyridin-4-yl-phenoxy)-phenyl]-acetic acid | pyridin-4-yl | 387.9 |
| 143 | [3,5-Dichloro-4-(4-hydroxy-3-pyrimidin-5-yl-phenoxy)-phenyl]-acetic acid | pyrimidin-5-yl | 388.8 |
| 144 | {3,5-Dichloro-4-[4-hydroxy-3-(4-methyl-pyridin-2-yl)-phenoxy]-phenyl}-acetic acid | 4-methyl-pyridin-2-yl | 402.0 |
| 145 | {3,5-Dichloro-4-[4-hydroxy-3-(6-methyl-pyridin-2-yl)-phenoxy]-phenyl}-acetic acid | 6-methyl-pyridin-2-yl | 402.0 |
| 146 | [3,5-Dichloro-4-(4-hydroxy-3-pyridin-2-yl-phenoxy)-phenyl]-acetic acid | pyridin-2-yl | 387.9 |
| 147 | [3,5-Dichloro-4-(4-hydroxy-3-thiazol-2-yl-phenoxy)-phenyl]-acetic acid | thiazol-2-yl | 393.9 |

Example 148

(S)-{3,5-Dibromo-4-[4-hydroxy-3-(4-phenyl-4,5-dihydro-oxazol-2-yl)-phenoxy]-phenyl}-acetic Acid

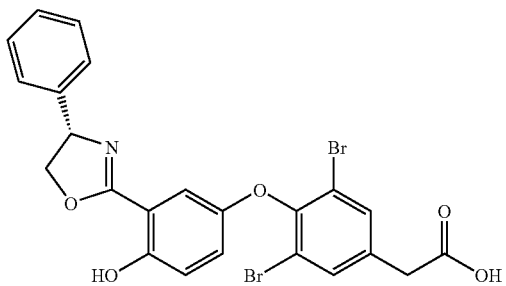

148A

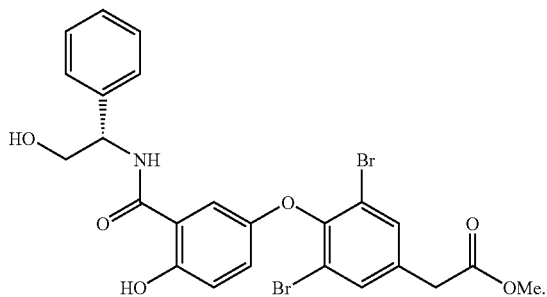

To a mixture containing S-phenylglycinol (35.4 mg, 0.258 mmol), compound 1E (92 mg, 0.2 mmol), HOAt (40.8 mg, 0.3 mmol), and 0.1 mL of DMF in 2 mL of dichloromethane was added diisopropylcarbodiimide (37.8 mg, 0.3 mmol). The reaction was stirred overnight at room temperature, then directly chromatographed on silica gel (1.8/8.2, EtOAc/toluene) to afford 62.3 mg (52% yield) of Compound 148A, with satisfactory 1H and 13C NMR.

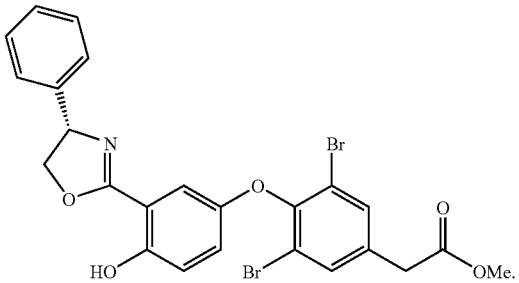

148B

To a mixture containing compound 148A (62.3 mg, 0.108 mmol) and triphenylphosphine (31.5 mg, 0.12 mmol) in 2 mL of tetrahydrofuran under argon was added diisopropylazodicarboxylate (24.3 mg, 0.12 mmol). The reaction mixture was concentrated in vacuo and chromatographed on silica gel (1/9, EtOAc/hexanes) to provide 22.3 mg (33% yield) of Compound 148B, with satisfactory 1H and 13C NMR spectra.

Example 148

Compound 148B (22.3 mg, 0.039 mmol) was dissolved in 0.3 mL of methanol and treated with 0.1 mL of 1N aq. NaOH. After 2 h, the reaction mixture was diluted with 1 mL of water, acidified with 0.05 mL of 2N aq. HCl, then concentrated to dryness in vacuo. The residue was taken up in 5 mL of ethyl acetate, filtered and the concentrated to dryness in vacuo to afford 7 mg (33% yield) of Example 148. Satisfactory 1H NMR and mass spectra (544, [M–H]$^-$) were obtained.

Examples 149 to 154

Examples 149 to 154 below, were also prepared by following procedures similar to those described above for Example 148.

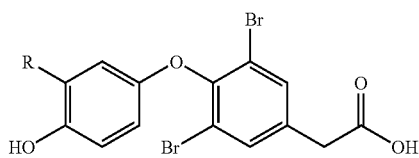

| Example | Name | R | [M – H]$^-$ |
|---|---|---|---|
| 149 | (R)-{3,5-Dibromo-4-[4-hydroxy-3-(4-isopropyl-4,5-dihydro-oxazol-2-yl)-phenoxy]-phenyl}-acetic acid | 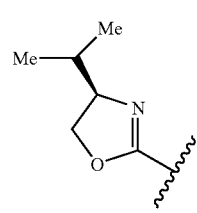 | 510 |

-continued

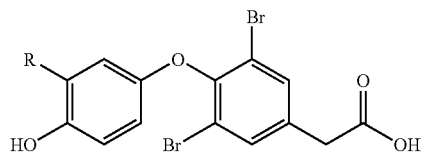

| Example | Name | R | [M − H]⁻ |
|---|---|---|---|
| 150 | (S)-{3,5-Dibromo-4-[4-hydroxy-3-(4-isopropyl-4,5-dihydro-oxazol-2-yl)-phenoxy]-phenyl}-acetic acid | | 510 |
| 151 | (R)-{3,5-Dibromo-4-[4-hydroxy-3-(4-phenyl-4,5-dihydro-oxazol-2-yl)-phenoxy]-phenyl}-acetic acid | | 544 |
| 152 | (R)-{3,5-Dibromo-4-[4-hydroxy-3-(4-methyl-4,5-dihydro-oxazol-2-yl)-phenoxy]-phenyl}-acetic acid | | 482 |
| 153 | (S)-{3,5-Dibromo-4-[4-hydroxy-3-(4-methyl-4,5-dihydro-oxazol-2-yl)-phenoxy]-phenyl}-acetic acid | | 482 |
| 154 | {3,5-Dibromo-4-[3-(4,5-dihydro-oxazol-2-yl)-4-hydroxy-phenoxy]-phenyl}-acetic acid | | 468 |

Example 155

{3,5-Dibromo-4-[4-hydroxy-3-(4-phenyl-oxazol-2-yl)-phenoxy]-phenyl}-acetic Acid

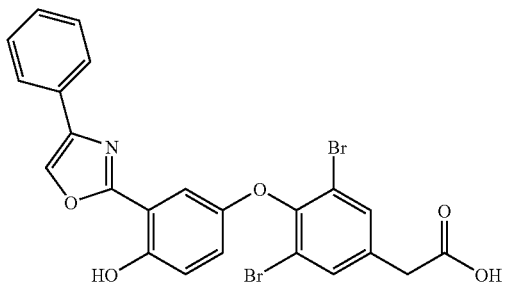

155A

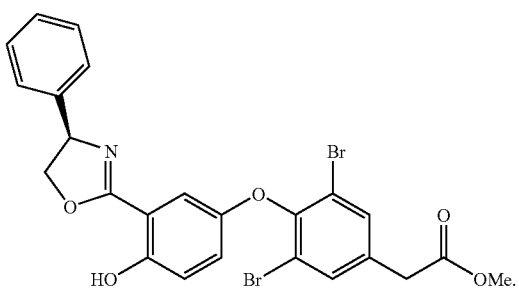

By following the procedure described for Compound 148B, Compound 155A was obtained with satisfactory 1H NMR.

155B

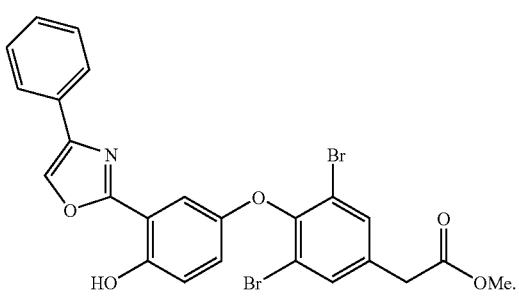

A mixture containing Compound 155A (11.9 mg, 0.021 mmol) and DDQ (6.8 mg, 0.03 mmol) in 0.5 mL of toluene was heated at 100° C. for 24 h. Purification by preparative TLC (silica gel; 3/7, EtOAc/hexanes) gave 7.5 mg (64% yield) of Compound 155B, satisfactory 1H NMR.

Example 155

Compound 155B (7.5 mg, 0.0134 mmol) was dissolved in a mixture of tetrahydrofuran (0.5 mL), methanol (0.2 mL), and 0.1 mL of 1N aq. NaOH and stirred for 4 h at room temperature. The reaction mixture was acidified and extracted with ethyl acetate. The organic extract was evaporated to dryness to provide 6.2 mg (85% yield) of Example 155, satisfactory 1H NMR and mass spectra (543.9, [M–H]⁻).

Example 156

{3,5-Dibromo-4-[4-hydroxy-3-(4-isopropyl-oxazol-2-yl)-phenoxy]-phenyl}-acetic Acid

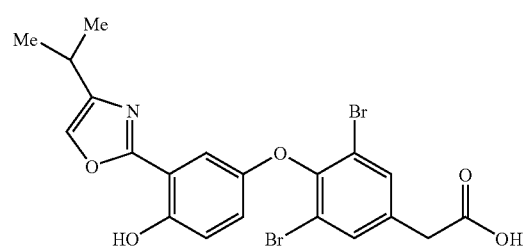

By following procedures similar to those described for Example 155, Example 156 was obtained, satisfactory 1H NMR and mass spectrum (508, [M–H]⁻).

Example 157

{3,5-Dibromo-4-[4-hydroxy-3-(4-methyl-oxazol-2-yl)-phenoxy]-phenyl}-acetic Acid

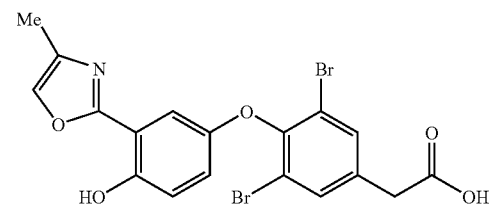

By following procedures similar to those described for Example 155, Example 157 was obtained, satisfactory 1H NMR and mass spectrum (481.9, [M–H]⁻).

Example 158

3,5-Dibromo-4-(6-hydroxy-5-isopropyl-biphenyl-3-yloxy)-benzoic Acid

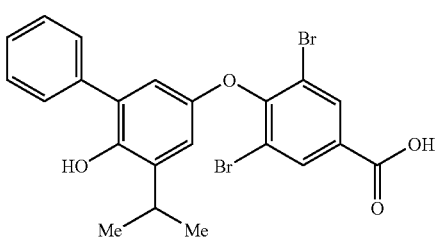

-continued

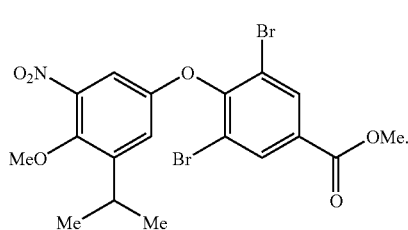
158A

Nitric acid (12 mmol, 0.82 mL, 65%) was added drop-wise to a well-stirred solution of 3,5-dibromo-4-(3-isopropyl-4-methoxyphenoxy)benzoate (2.0 mmol, 916 mg; prepared as described in Li et al, PCT WO 9900353 A1) in benzene (150 mL). The resulting mixture were stirred at room temperature for an hour and then treated with saturated aqueous sodium hydroncarbonate (10 mL). The organic phase was separated, the aqueous phase was additionally extracted with chloroform (2×20 mL). The combined organic phases were evaporated in vacuo and the residue crystallized from ethanol (80%), to give 912 mg (91%) of Compound 158A.

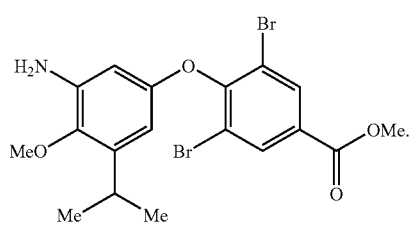
158B

A mixture of Compound 158A (2.82 mmol, 1.42 g) and sodium hydrosulfite (Na$_2$S$_2$O$_4$, 14.1 mmol, 2.90 g, 85%) in ethanol (150 mL, 95.5%) were stirred at 70° C. for 18 hours. The reaction mixture was concentrated, water (50 mL) and saturated aqueous sodium hydroncarbonate solution (50 mL) was added to the residue. The reaction mixture was extracted with ethyl acetate (5×25 mL), the combined extracts washed with brine, dried with anhydrous sodium sulfate and concentrated in vacuo. The residue was dissolved in diethyl ether (10 mL) and triturated with iso-hexane (30 mL) at 0° C. This gave 1.23 g (92%) of Compound 158B.

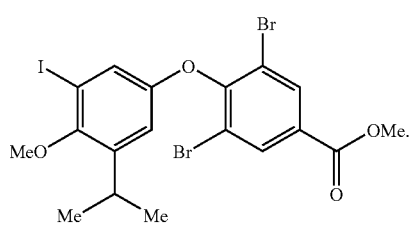
158C

A solution of sodium nitrite (3.0 mmol, 207 mg) in water (5 mL) was added to a well-stirred solution of Compound 158B (2.0 mmol, 946 mg) in a mixture of methanol (40 mL) and hydrochloric acid (40 mL, 37%) under cooling to −15° C. The reaction mixture was stirred for an hour at the same temperature and then a solution of potassium iodide (6.0 mmol, 996 mg) in water (5 mL) was added. The reaction mixture was stirred for 30 minutes between −15° C. and −10° C. The reaction mixture was extracted with chloroform (5×25 mL), and the combined extracts washed with saturated aqueous sodium bicarbonate followed by a solution of saturated aqueous sodium thiosulfate. The organic phase was dried over anhydrous sodium sulfate and concentrated in vacuo. The residue was recrystallized from ethanol (80%), to give 874 mg (75%) of Compound C.

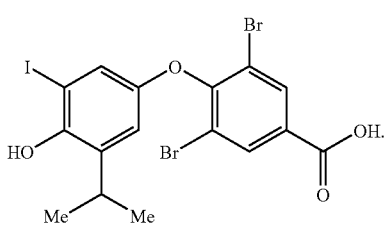
158D

A mixture of Compound 158C (0.685 mmol, 400 mg) and potassium hydroxide (2 mmol, 2 mL, 1N) in ethanol (20 mL, 95.5%) was stirred at 70° C. for one hour. The solvent was evaporated in vacuo and the residue was acidified with hydrochloric acid (5 mL of 1N). The product was extracted with chloroform (5×10 mL), the combined extracts dried over anhydrous sodium sulphate and concentrated in vacuo. The residue was diluted with dichloromethane (50 mL) and boron trifluoride dimethyl sulfide complex (13.7 mmol, 1.78 g) was added drop-wise. The reaction mixture was stirred at room temperature for 18 hours and then treated with water (30 mL). The organic phase was separated and the aqueous phase extracted with chloroform (4×15 mL). The combined extracts were concentrated in vacuo and the residue triturated by addition of iso-hexane. This gave 345 mg (91%) of Compound 158D.

Example 158

A mixture of Compound 158D (0.20 mmol, 111 mg), benzeneboronic acid (0.30 mmol, 37 mg), tris(dibenzylideneacetone)-dipalladium (0.020 mmol, 18 mg) and potassium carbonate (0.60 mmol, 0.60 mL, 1N) in dioxane (5 mL) was placed in a Heck-vial and nitrogen was bubbled through the mixture for 5 min. The vial was sealed and the reaction mixture stirred at 70° C. for 1 hour and then at 120° C. for 18 hours. The reaction mixture was concentrated in vacuo, the residue acidified with hydrochloric acid (2 mL, 1N) and extracted with chloroform (4×5 mL). The combined extracts were concentrated in vacuo and purified on column (silica gel, chloroform/methanol, 9:1) to give 70 mg (69%) of Example 158, LC-MS (ES): m/z 505 (M−1).

Example 159

3-[3,5-Dibromo-4-(6-hydroxy-5-isopropyl-biphenyl-3-yloxy)-phenyl]-propionic Acid

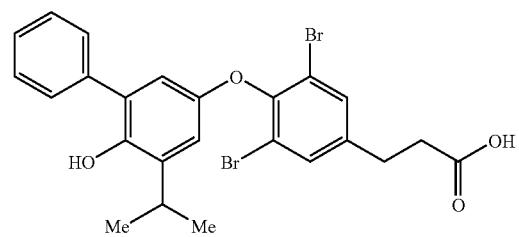

By following procedures similar to those described for Example 158, Example 159 was obtained, LC-MS (ES): m/z 533 (M−1).

Example 160

3,5-Dibromo-4-(3-furan-2-yl-4-hydroxy-5-isopropyl-phenoxy)-benzoic Acid

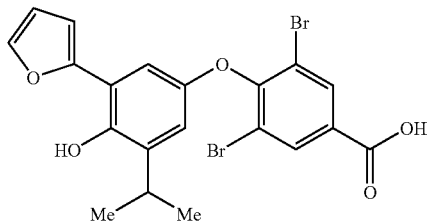

By following procedures similar to those described for Example 158, Example 160 was obtained, LC-MS (ES): m/z 533 (M−1).

Example 161

{2-[3,5-DICHLORO-4-(6-HYDROXY-3'-METHYL-BIPHENYL-3-YLOXY)-phenyl]-acetylamino}-acetic Acid

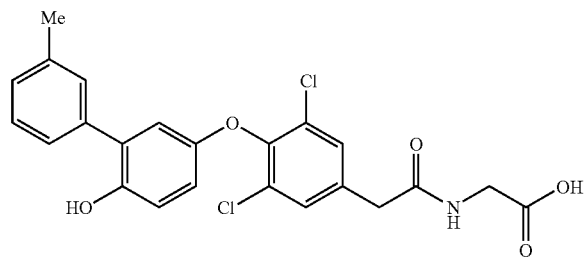

By following procedures similar to those described for Examples 99 to 101, Example 161 was obtained and characterized by satisfactory 1H and 13C NMR and mass spectra (458, [M−H]−).

Example 162

(S)-2-{2-[3,5-Dichloro-4-(6-hydroxy-3'-methyl-biphenyl-3-yloxy)-phenyl]-acetylamino}-3-methyl-butyric Acid

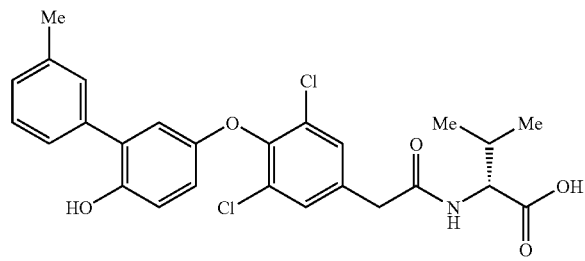

By following procedures similar to those described for Examples 99 to 101, Example 162 was obtained and characterized by satisfactory 1H and 13C NMR and mass spectra (500, [M−H]−).

Example 163

(R)-2-{2-[3,5-Dichloro-4-(6-hydroxy-3'-methyl-biphenyl-3-yloxy)-phenyl]-acetylamino}-3-methyl-butyric Acid

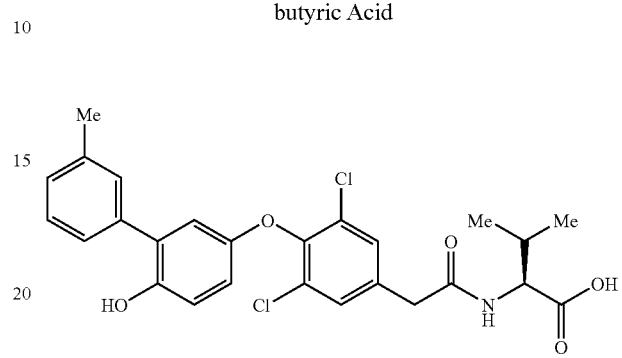

By following procedures similar to those described for Examples 99 to 101, Example 163 was obtained and characterized by satisfactory 1H and 13C NMR and mass spectra (500, [M−H]−).

Example 164

[3,5-Dichloro-4-(6-hydroxy-biphenyl-3-yloxy)-benzoylamino]-acetic Acid

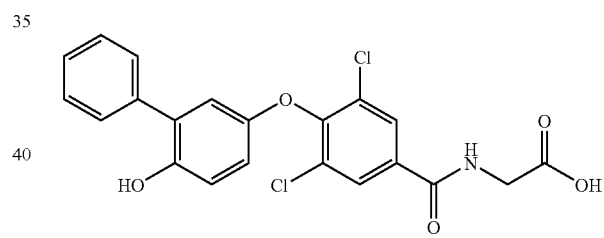

By following procedures similar to those described for Examples 99 to 101, Example 164 was obtained and characterized by satisfactory 1H and 13C NMR and mass spectra (430, [M−H]−).

Example 165

[3,5-Dichloro-4-(6-hydroxy-3'-methoxy-biphenyl-3-yloxy)-benzoylamino]-acetic Acid

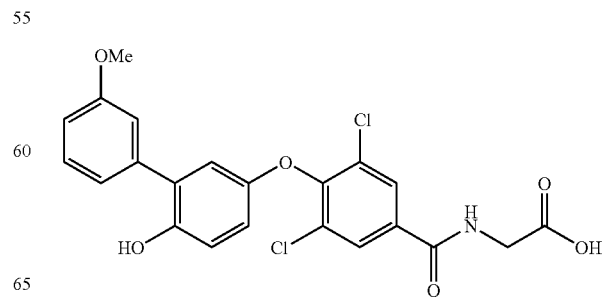

By following procedures similar to those described for Examples 99 to 101, Example 165 was obtained and characterized by satisfactory 1H and 13C NMR spectra.

Example 166

[3,5-Dichloro-4-(6-hydroxy-biphenyl-3-yloxy)-benzyl]-phosphonic Acid Monoethyl Ester

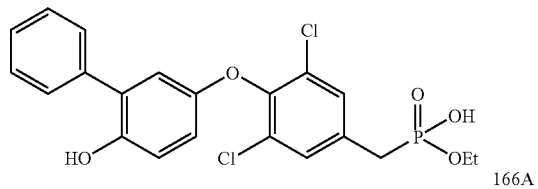

166A

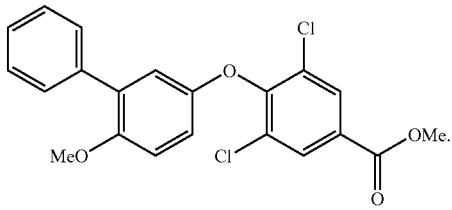

Compound 166A was prepared by procedures similar to those described for Examples 99 to 100. The isolated product exhibited satisfactory 1H and 13C NMR spectra.

166B

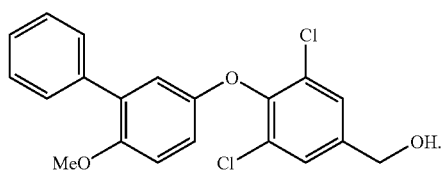

Compound 166A (528 mg, 1.31 mmol) in 13 mL of THF cooled to −78° C. was treated with a 1.0 M solution of diisobutylaluminum hydride in toluene (13.1 mL, 13.1 mmol). The reaction was kept at −78° C. for 6 h, then carefully quenched with 1N aq HCl. The product was extracted with ethyl acetate and the organic extract rinsed with three 25 mL portions of brine, dried (MgSO4) and concentrated in vacuo. Chromatography on silica gel (30% EtOAc in hexanes) gave 425 mg (86% yield) of Compound 166B, satisfactory 1H NMR and mass spectrum.

166C

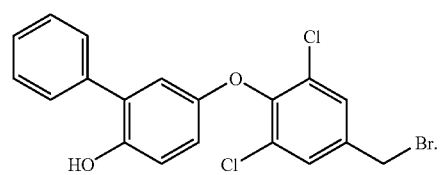

To a solution of Compound 166B (412 mg, 1.09 mmol) in 10 mL of methylene chloride was added boron tribromide (466 mg, 1.10 mmol). The reaction was allowed to warm to room temperature, then stirred for 3 h and poured into a vigorously stirred mixture of ethyl acetate (100 mL) and saturated aqueous sodium bicarbonate (50 mL). The organic layer was separated and rinsed with brine, dried (MgSO4) and concentrated in vacuo. Chromatography on silica gel (15% EtOAc in hexanes) afforded 412 mg (88% yield ) of Compound 166C, satisfactory 1H NMR and mass spectrum.

166D

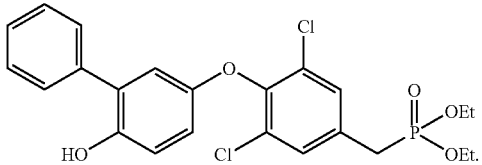

A solution of Compound 166C (100 mg, 0.236 mmol), triethyl phosphite (3 mL) and toluene (3 mL) was heated at 130° C. for 18 h, then cooled to room temperature and concentrated in vacuo. Chromatographic purification gave 76 mg (67% yield) of Compound 166D, satisfactory 1H NMR and mass spectrum.

Example 166

To a solution of Compound 166D (45 mg, 0.0935 mmol) in ethanol (1 ML) was added 1N aq sodium hydroxide (0.374 mL). The reaction mixture was refluxed for 1.5 h, then treated with a further 0.2 mL of 1N aq sodium hydroxide a refluxed for a total of 3.5 h. The reaction mixture was cooled to room temperature, then acidified with 1N aq HCl and extracted with ethyl acetate. The crude product was purified by preparative reverse phase chromatography on a YMC S5 ODS 20×100 mm column eluted with a gradient from 10:90:0.1, methanol:water:TFA to 90:10:0.1, methanol:water:TFA. Example 166 was obtained as a white, powdery solid (32.3 mg, 76% yield), 1H NMR and mass spectrum (451, [M−H]−).

Example 167

[3,5-Dichloro-4-(6-hydroxy-biphenyl-3-yloxy)-benzyl]-methyl-phosphinic Acid

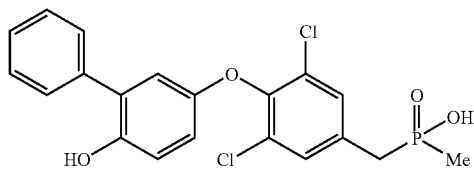

167A

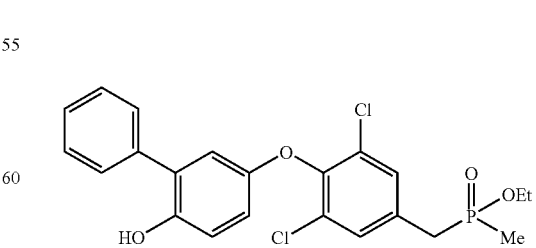

To a slurry of Compound 166C (100 mg, 0.236 mmol) in toluene (3 mL) was added diethyl methylphosphonite (0.5 mL). The mixture was heated at 110° C. for 15 h, then cooled to room temperature and purified by preparative reverse phase HPLC on a YMC S5 ODS 20×100 mm column eluted with a gradient from 10:90:0.1, methanol:water:TFA to 90:10:0.1, methanol:water:TFA to give 70 mg. (66% yield) of Compound 167A, satisfactory 1H NMR and mass spectrum.

Example 167

To a solution containing Compound 167A (50 mg, 0.111 mmol) in ethanol (0.5 mL) was added 6N aq HCl (4 mL). The reaction mixture was refluxed for 6 h, then cooled to room temperature and extracted with ethyl acetate. The crude product was purified by preparative reverse phase HPLC on a YMC S5 ODS 20×100 mm column eluted with a gradient from 10:90:0.1, methanol:water:TFA to 90:10:0.1, methanol:water:TFA to give 29 mg (62% yield) of Example 167, satisfactory 1H NMR and mass spectrum (421, [M–H]⁻).

Example 168

5-[2,6-Dichloro-4-(1H-tetrazol-5-ylmethyl)-phenoxy]-biphenyl-2-ol

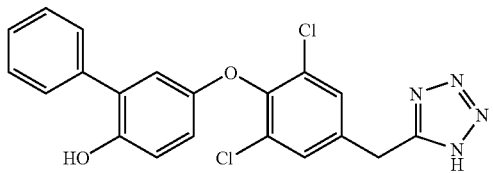

168A

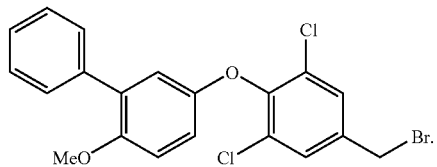

Compound 168A was obtained by following procedure similar to those described for Examples 99 to 100 and Example 166C, satisfactory 1H NMR and mass spectrum.

168B

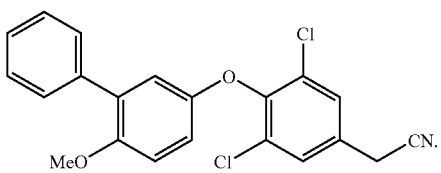

A solution of Compound 168A (180 mg, 0.411 mmol) and sodium cyanide (40.3 mg, 0.822 mmol) in a mixture of dimethylformamide (2 mL) and methanol (5 mL) was heated to 70° C. for 30 minutes. The reaction mixture was cooled to room temperature and chromatographed on silica gel (15% EtOAc in hexanes) to give 45 mg (28% yield) of Compound 168B, satisfactory 1H NMR and mass spectrum.

168C

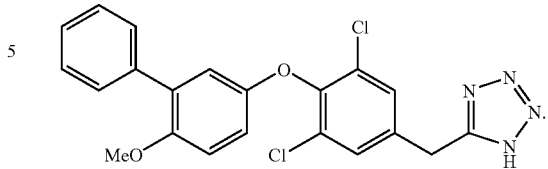

A mixture of Compound 168B (40 mg, 0.104 mmol) and azidotrimethylsilane (32 mg, 0.156 mmol) in toluene (5 mL) was heated at 100° C. for 15 h, then treated with an additional 21 mg of azidotrimethylsilane and heated at 100° C. for another 7 hours. The reaction mixture was cooled to room temperature and the preparative reverse phase HPLC on a YMC S5 ODS 20×100 mm column eluted with a gradient from 10:90:0.1, methanol:water:TFA to 90:10:0.1, methanol:water:TFA to give 34 mg (76% yield) of Compound 168C, satisfactory 1H NMR and mass spectrum.

Example 168

To a solution of Compound 168C (25 mg, 0.0585 mmol) in dichloromethane (2 mL) cooled in an ice-water bath was added boron tribromide (0.6 mL of 1.0M in dichloromethane). The reaction was allowed to warm to room temperature, and after 2 h the reaction mixture was poured into an ice-water mixture (20 mL) and extracted with ethyl acetate. The ethyl acetate extract was rinsed with brine, dried (MgSO4) and concentrated in vacuo to provide 42 mg of crude product. Preparative reverse phase HPLC on a YMC S5 ODS 20×100 mm column eluted with a gradient from 10:90:0.1, methanol:water:TFA to 90:10:0.1, methanol:water:TFA gave 5.3 mg (22% yield) of Example 168, satisfactory 1H NMR and mass spectrum (411, [M–H]⁻).

What is claimed is:

1. A compound of the following formula

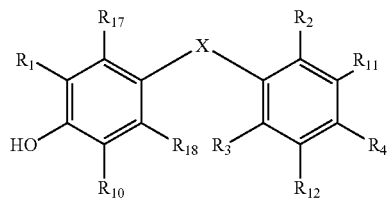

wherein
R1 is

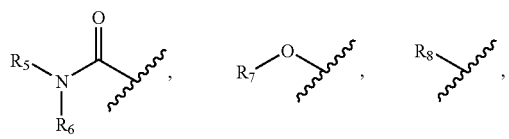

R2 and R3 are the same or different and are bromine, chlorine or methyl;

R4 is

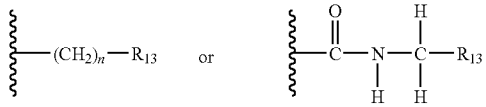

and n is 1 or 2;

One of $R^5$ and $R^6$ is hydrogen and the other is alkyl or aralkyl;

$R^7$ is aryl, alkyl, or aralkyl;

$R^8$ is aryl or cycloalkyl;

$R^{10}$ is hydrogen;

One of $R^{11}$ and $R^{12}$ is hydrogen and the other is either hydrogen or methyl;

$R^{13}$ is carboxyl;

$R^{17}$ and $R^{18}$ are hydrogen; and

X is oxygen (—O—), sulfur (—S—) or methylene (—CH$_2$—).

2. A pharmaceutical composition which functions as a selective agonist of the thyroid hormone receptor-beta comprising a compound as defined in claim 1.

3. A pharmaceutical composition comprising a compound as defined in claim 1 and a pharmaceutically acceptable carrier therefor.

4. A pharmaceutical composition comprising at least one compound as defined in claim 1 and at least one additional therapeutic agent selected from the group consisting of antidiabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

5. The pharmaceutical composition of claim 4 wherein said additional therapeutic agent is an antidiabetic agent selected from the group consisting of a biguanide, a glucosidase inhibitor, a meglitinide, a sulfonylurea, a thiazolidinedione, a PPAR-alpha agonist, a PPAR-gamma agonist, a PPAR alpha/gamma dual agonist, an SGLT2 inhibitor, a glycogen phosphorylase inhibitor, an aP2 inhibitor, a dipeptidyl peptidase IV inhibitor and insulin.

6. The pharmaceutical composition of claim 4 wherein said additional therapeutic agent is an antidiabetic agent selected from the group consisting of metformin, glyburide, glimepiride, glipyride, glipizide, chlorpropamide, gliclazide, acarbose, miglitol, troglitazone, pioglitazone, englitazone, darglitazone, rosiglitazone and insulin.

7. The pharmaceutical composition of claim 4 wherein said additional therapeutic agent is an anti-obesity agent is selected from the group consisting of an aP2 inhibitor, a PPAR gamma antagonist, a PPAR delta agonist, a beta 3 adrenergic agonist, a lipase inhibitor, a serotonin reuptake inhibitor, a cannabinoid-1 receptor antagonist and an anorectic agent.

8. The pharmaceutical composition of claim 4 wherein said additional therapeutic agent is a hypolipidemic agent selected from the group consisting of a thiazolidinedione, an MTP inhibitor, a squalene synthetase inhibitor, an HMG CoA reductase inhibitor, a fibric acid derivative, an ACAT inhibitor, a cholesterol absorption inhibitor, an ileal Na$^+$/bile cotransporter inhibitor, a bile acid sequestrant and a nicotinic acid.

9. A compound selected from the group consisting of:
[3,5-Dibromo-4-(4-hydroxy-3-phenethylcarbamoyl-phenoxy)-phenyl]-acetic acid;
[3,5-Dichloro-4-(4-hydroxy-3-phenethylcarbamoyl-phenoxy)-phenyl]-acetic acid;
[4-(3-Benzylcarbamoyl-4-hydroxy-phenoxy)-3,5-dibromo-phenyl]-acetic acid;
[5-(2,6-Dibromo-4-carboxymethyl-phenoxy)-2-hydroxy-benzoylamino]-acetic acid;
[3,5-Dibromo-4-(4-hydroxy-3-phenylcarbamoyl-phenoxy)-phenyl]-acetic acid;
{3,5-Dibromo-4-[4-hydroxy-3-(4-phenyl-butylcarbamoyl)-phenoxy]phenyl}acetic acid;
{3,5-Dibromo-4-[4-hydroxy-3-(3-phenyl-propylcarbamoyl)-phenoxy]-phenyl}-acetic acid;
(S)-{3,5-Dibromo-4-[4-hydroxy-3-(2-hydroxy-1-phenyl-ethylcarbamoyl)-phenoxy]-phenyl}-acetic acid;
(R)-{3,5-Dibromo-4-[4-hydroxy-3-(2-hydroxy-1-phenyl-ethylcarbamoyl)-phenoxy]-phenyl}-acetic acid;
(R)-{3,5-Dibromo-4-[4-hydroxy-3-(2-hydroxy-2-phenyl-ethylcarbamoyl)-phenoxy]-phenyl}-acetic acid;
(S)-{3,5-Dibromo-4-[4-hydroxy-3-(3-hydroxy-3-phenyl-propylcarbamoyl)-phenoxy]-phenyl}-acetic acid;
(R)-{3,5-Dibromo-4-[4-hydroxy-3-(3-hydroxy-3-phenyl-propylcarbamoyl)-phenoxy]-phenyl}-acetic acid;
(S)-{3,5-Dibromo-4-[4-hydroxy-3-(2-hydroxy-2-phenyl-ethylcarbamoyl)-phenoxy]-phenyl}-acetic acid;
(R)-{3,5-Dibromo-4-[4-hydroxy-3-(1-hydroxymethyl-2-methyl-propylcarbamoyl)-phenoxy]-phenyl}-acetic acid;
(S)-{3,5-Dibromo-4-[4-hydroxy-3-(1-hydroxymethyl-2-methyl-propylcarbamoyl)-phenoxy]-phenyl}-acetic acid;
(S)-{3,5-Dibromo-4-[4-hydroxy-3-(2-hydroxy-1-methyl-ethylcarbamoyl)-phenoxy]-phenyl}-acetic acid;
(R)-{3,5-Dibromo-4-[4-hydroxy-3-(2-hydroxy-1-methyl-ethylcarbamoyl)-phenoxy]-phenyl}-acetic acid;
{3,5-Dibromo-4-[4-hydroxy-3-(indan-2-ylcarbamoyl)-phenoxy]-phenyl}-acetic acid;
{3,5-Dibromo-4-[3-(cyclohexylmethyl-carbamoyl)-4-hydroxy-phenoxy]-phenyl}-acetic acid;
(3,5-Dibromo-4-{4-hydroxy-3-[2-(4-methoxy-phenyl)-ethylcarbamoyl]-phenoxy}-phenyl)-acetic acid;
{3,5-Dibromo-4-[4-hydroxy-3-(3-methyl-benzylcarbamoyl)-phenoxy]-phenyl}-acetic acid;
(3,5-Dibromo-4-{4-hydroxy-3-[2-(3-methoxy-phenyl)-ethylcarbamoyl]phenoxy}-phenyl)-acetic acid;
(R)-{3,5-Dibromo-4-[4-hydroxy-3-(1-phenyl-propylcarbamoyl)-phenoxy]-phenyl}-acetic acid;
(3,5-Dibromo-4-{4-hydroxy-3-[2-(2-methoxy-phenyl)-ethylcarbamoyl]-phenoxy}-phenyl)-acetic acid;
{3,5-Dibromo-4-[4-hydroxy-3-(2-phenyl-cyclopropylcarbamoyl)-phenoxy]-phenyl}-acetic acid (racemic, trans);
(S)-{3,5-Dibromo-4-[4-hydroxy-3-(1-phenyl-propylcarbamoyl)-phenoxy]-phenyl}-acetic acid;
(3,5-Dibromo-4-{4-hydroxy-3-[2-(4-phenoxy-phenyl)-ethylcarbamoyl]-phenoxy}-phenyl)-acetic acid;
(R)-{3,5-Dibromo-4-[4-hydroxy-3-(1-phenyl-ethylcarbamoyl)-phenoxy]-phenyl}-acetic acid;
{3,5-Dibromo-4-[4-hydroxy-3-(2-methoxy-benzylcarbamoyl)-phenoxy]-phenyl}-acetic acid;
(3,5-Dibromo-4-{4-hydroxy-3-[(naphthalen-1-ylmethyl)-carbamoyl]-phenoxy}-phenyl)-acetic acid;
(S)-{3,5-Dibromo-4-[4-hydroxy-3-(1-phenyl-ethylcarbamoyl)-phenoxy]-phenyl}-acetic acid;
{3,5-Dibromo-4-[3-(3-fluoro-benzylcarbamoyl)-4-hydroxy-phenoxy]-phenyl}-acetic acid;
{3,5-Dibromo-4-[4-hydroxy-3-(4-methoxy-benzylcarbamoyl)-phenoxy]-phenyl}-acetic acid;

{3,5-Dibromo-4-[3-(3,5-difluoro-benzylcarbamoyl)-4-hydroxy-phenoxy]-phenyl}-acetic acid;
{3,5-Dibromo-4-[4-hydroxy-3-(3-trifluoromethyl-benzylcarbamoyl)-phenoxy]-phenyl}-acetic acid;
{3,5-Dibromo-4-[3-(3,4-difluoro-benzylcarbamoyl)-4-hydroxy-phenoxy]-phenyl}-acetic acid;
(3,5-Dibromo-4-{3-[2-(3,4-dimethoxy-phenyl)-ethylcarbamoyl]-4-hydroxy-phenoxy}-phenyl)-acetic acid;
{3,5-Dibromo-4-[4-hydroxy-3-(4-trifluoromethyl-benzylcarbamoyl)-phenoxy]-phenyl}-acetic acid;
{3,5-Dibromo-4-[3-(2,3-dimethyl-benzylcarbamoyl)-4-hydroxy-phenoxy]-phenyl}-acetic acid;
{3,5-Dibromo-4-[3-(3,5-dimethyl-benzylcarbamoyl)-4-hydroxy-phenoxy]-phenyl}-acetic acid;
{3,5-Dibromo-4-[4-hydroxy-3-(3-methoxy-benzylcarbamoyl)-phenoxy]-phenyl}-acetic acid;
{3,5-Dibromo-4-[4-hydroxy-3-(2-methyl-benzylcarbamoyl)-phenoxy]-phenyl}-acetic acid;
{3,5-Dibromo-4-[4-hydroxy-3-(2-trifluoromethyl-benzylcarbamoyl)-phenoxy]-phenyl}-acetic acid;
{4-[3-(Benzyl-methyl-carbamoyl)-4-hydroxy-phenoxy]-3,5-dibromo-phenyl}-acetic acid;
{3,5-Dibromo-4-[4-hydroxy-3-(4-methyl-benzylcarbamoyl)-phenoxy]-phenyl}-acetic acid;
{3,5-Dibromo-4-[3-(3-chloro-4-fluoro-benzylcarbamoyl)-4-hydroxy-phenoxy]-phenyl}-acetic acid;
{3,5-Dibromo-4-[3-(2-fluoro-benzylcarbamoyl)-4-hydroxy-phenoxy]-phenyl}-acetic acid;
(3,5-Dibromo-4-{3-[2-(2-fluoro-phenyl)-ethylcarbamoyl]-4-hydroxy-phenoxy}-phenyl)-acetic acid;
{3,5-Dibromo-4-[3-(2,2-diphenyl-ethylcarbamoyl)-4-hydroxy-phenoxy]-phenyl}-acetic acid;
{3,5-Dibromo-4-[3-(2-chloro-4-fluoro-benzylcarbamoyl)-4-hydroxy-phenoxy]-phenyl}-acetic acid;
{3,5-Dibromo-4-[3-(2-chloro-6-fluoro-benzylcarbamoyl)-4-hydroxy-phenoxy]-phenyl}-acetic acid;
{3,5-Dibromo-4-[3-(2,5-difluoro-benzylcarbamoyl)-4-hydroxy-phenoxy]-phenyl}-acetic acid;
{3,5-Dibromo-4-[3-(2,4-difluoro-benzylcarbamoyl-4-hydroxy-phenoxy]-phenyl}-acetic acid;
(3,5-Dibromo-4-{4-hydroxy-3-[2-(4-nitro-phenyl)-ethylcarbamoyl]-phenoxy}-phenyl)-acetic acid;
(3,5-Dibromo-4-{3-[2-(4-fluoro-phenyl)-ethylcarbamoyl]-4-hydroxy-phenoxy}-phenyl)-acetic acid;
{3,5-Dibromo-4-[3-(3,4-dimethyl-benzylcarbamoyl)-4-hydroxy-phenoxy]-phenyl}-acetic acid;
{3,5-Dibromo-4-[3-(4-fluoro-benzylcarbamoyl)-4-hydroxy-phenoxy]-phenyl}-acetic acid;
{3,5-Dibromo-4-[4-hydroxy-3-(3-phenyl-propionylamino)-phenoxy]-phenyl}-acetic acid;
{3,5-Dibromo-4-[4-hydroxy-3-(4-trifluoromethyl-phenoxy)-phenoxy]-phenyl}-acetic acid;
[3,5-Dichloro-4-(4-hydroxy-3-phenoxy-phenoxy)-phenyl]-acetic acid;
{3,5-Dichloro-4-[4-hydroxy-3-(4-hydroxy-phenoxy)-phenoxy]-phenyl}-acetic acid;
{3,5-Dibromo-4-[3-(3,5-dichloro-phenoxy)-4-hydroxy-phenoxy]-phenyl}-acetic acid;
[3,5-Dibromo-4-(4-hydroxy-3-p-tolyloxy-phenoxy)-phenyl]-acetic acid;
{3,5-Dibromo-4-[3-(4-chloro-phenoxy)-4-hydroxy-phenoxy]-phenyl}-acetic acid;
{3,5-Dibromo-4-[3-(4-fluoro-phenoxy)-4-hydroxy-phenoxy]-phenyl}-acetic acid;
[3,5-Dibromo-4-(4-hydroxy-3-phenoxy-phenoxy)-phenyl]-acetic acid;
{3,5-Dibromo-4-[4-hydroxy-3-(naphthalen-1-yloxy)-phenoxy]-phenyl}-acetic acid;
{3,5-Dibromo-4-[4-hydroxy-3-(2-trifluoromethyl-phenoxy)-phenoxy]-phenyl}-acetic acid;
{4-[3-(Biphenyl-4-yloxy)-4-hydroxy-phenoxy]-3,5-dibromo-phenyl}-acetic acid;
{4-[3-(Biphenyl-3-yloxy)-4-hydroxy-phenoxy]-3,5-dibromo-phenyl}-acetic acid;
{3,5-Dibromo-4-[4-hydroxy-3-(4-isopropyl-phenoxy)-phenoxy]-phenyl}-acetic acid;
{3,5-Dibromo-4-[4-hydroxy-3-(4-methyl-3-nitro-phenoxy)-phenoxy]-phenyl}-acetic acid;
{3,5-Dibromo-4-[4-hydroxy-3-(naphthalen-2-yloxy)-phenoxy]-phenyl}-acetic acid;
{3,5-Dibromo-4-[4-hydroxy-3-(2-hydroxy-phenoxy)-phenoxy]-phenyl}-acetic acid;
{3,5-Dibromo-4-[4-hydroxy-3-(4-hydroxy-phenoxy)-phenoxy]-phenyl}-acetic acid;
{3,5-Dibromo-4-[4-hydroxy-3-(3-hydroxy-phenoxy)-phenoxy]-phenyl}-acetic acid;
{3,5-Dibromo-4-[3-(2,3-dichloro-phenoxy)-4-hydroxy-phenoxy]-phenyl}-acetic acid;
{3,5-Dibromo-4-[3-(3,4-dichloro-phenoxy)-4-hydroxy-phenoxy]-phenyl}-acetic acid;
{3,5-Dibromo-4-[3-(2,4-dichloro-phenoxy)-4-hydroxy-phenoxy]-phenyl}-acetic acid;
{3,5-Dibromo-4-[3-(3-fluoro-phenoxy)-4-hydroxy-phenoxy]-phenyl}-acetic acid;
[3-Bromo-4-(4-hydroxy-3-phenoxy-phenoxy)-5-methyl-phenyl]-acetic acid;
{3,5-Dibromo-4-[3-(4-butyl-phenoxy)-4-hydroxy-phenoxy]-phenyl}-acetic acid;
{3,5-Dibromo-4-[4-hydroxy-3-(3-trifluoromethyl-phenoxy)-phenoxy]-phenyl}-acetic acid;
{35-Dibromo-4-[3-(3-chloro-4-fluoro-phenoxy)-4-hydroxy-phenoxy]-phenyl}-acetic acid;
{3,5-Dichloro-4-[3-(3,5-dichloro-phenoxy)-4-hydroxy-phenoxy]-phenyl}-acetic acid;
{3,5-Dibromo-4-[4-hydroxy-3-(4-trifluoromethoxy-phenoxy)-phenoxy]-phenyl}-acetic acid;
{3,5-Dibromo-4-[3-(4-fluoro-phenoxy)-4-hydroxy-phenoxy]-phenyl}-acetic acid;
[3,5-Dichloro-4-(4-hydroxy-3-p-tolyloxy-phenoxy)-phenyl]-acetic acid;
{3,5-Dichloro-4-[4-hydroxy-3-(4-trifluoromethyl-phenoxy)-phenoxy]-phenyl}-acetic acid;
{3,5-Dichloro-4-[3-(4-fluoro-phenoxy)-4-hydroxy-phenoxy]-phenyl}-acetic acid;
{3,5-Dichloro-4-[4-hydroxy-3-(2-trifluoromethyl-phenoxy)-phenoxy]-phenyl}-acetic acid;
[3,5-Dichloro-4-(6-hydroxy-biphenyl-3-yloxy)-phenyl]-acetic acid;
[3,5-Dichloro-4-(6-hydroxy-4'-trifluoromethyl-biphenyl-3-yloxy)-phenyl]-acetic acid;
[3,5-Dichloro-4-(3'-ethyl-6-hydroxy-biphenyl-3-yloxy)-phenyl]-acetic acid;
[3,5-Dichloro-4-(6,3'-dihydroxy-biphenyl-3-yloxy)-phenyl]-acetic acid
[4-(3'-Carbamoyl-6-hydroxy-biphenyl-3-yloxy)-3,5-dichloro-phenyl]-acetic acid;
[4-(4'-Carbamoyl-6-hydroxy-biphenyl-3-yloxy)-3,5-dichloro-phenyl]-acetic acid;
[3,5-Dichloro-4-(6-hydroxy-2'-hydroxymethyl-biphenyl-3-yloxy)-phenyl]-acetic acid;
[3,5-Dichloro-4-(6-hydroxy-4'-methyl-biphenyl-3-yloxy)-phenyl]-acetic acid;

[3,5-Dichloro-4-(6-hydroxy-3'-methyl-biphenyl-3-yloxy)-phenyl]-acetic acid;

[3,5-Dichloro-4-(6-hydroxy-2'-trifluoromethyl-biphenyl-3-yloxy)-phenyl]-acetic acid;

[3,5-Dichloro-4-(6,4'-dihydroxy-biphenyl-3-yloxy)-phenyl]-acetic acid;

[3,5-Dichloro-4-(6-hydroxy-3'-trifluoromethyl-biphenyl-3-yloxy)-phenyl]-acetic acid;

[3,5-Dichloro-4-(4'-fluoro-6-hydroxy-biphenyl-3-yloxy)-phenyl]-acetic acid;

[3,5-Dichloro-4-(6-hydroxy-[1,1';4',1'']terphenyl-3-yloxy)-phenyl]-acetic acid;

[3,5-Dichloro-4-(6-hydroxy-[1,1';3',1'']terphenyl-3-yloxy)-phenyl]-acetic acid;

[3,5-Dichloro-4-(6,2'-dihydroxy-biphenyl-3-yloxy)-phenyl]-acetic acid;

[3,5-Dichloro-4-(6-hydroxy-2',4'-dimethyl-biphenyl-3-yloxy)-phenyl]-acetic acid;

[3,5-Dichloro-4-(6-hydroxy-2',3'-dimethyl-biphenyl-3-yloxy)-phenyl]-acetic acid;

[3,5-Dichloro-4-(6-hydroxy-3',5'-dimethyl-biphenyl-3-yloxy)-phenyl]-acetic acid;

[3,5-Dichloro-4-(6-hydroxy-3',4'-dimethyl-biphenyl-3-yloxy)-phenyl]-acetic acid;

[3,5-Dichloro-4-(6-hydroxy-2',5'-dimethyl-biphenyl-3-yloxy)-phenyl]-acetic acid;

[3,5-Dichloro-4-(3'-chloro-6-hydroxy-biphenyl-3-yloxy)-phenyl]-acetic acid;

[3,5-Dichloro-4-(3'-fluoro-6-hydroxy-biphenyl-3-yloxy)-phenyl]-acetic acid;

[4-(3'-Acetyl-6-hydroxy-biphenyl-3-yloxy)-3,5-dichloro-phenyl]-acetic acid;

[3,5-Dichloro-4-(6-hydroxy-4'-phenoxy-biphenyl-3-yloxy)-phenyl]-acetic acid;

[4-(5'-tert-Butyl-6-hydroxy-2'-methyl-biphenyl-3-yloxy)-3,5-dichloro-phenyl]-acetic acid;

[3,5-Dichloro-4-(6-hydroxy-2',4',5'-trimethyl-biphenyl-3-yloxy)-phenyl]-acetic acid;

[3,5-Dichloro-4-(6-hydroxy-3'-propyl-biphenyl-3-yloxy)-phenyl]-acetic acid;

[3,5-Dichloro-4-(6-hydroxy-3'-isobutyl-biphenyl-3-yloxy)-phenyl]-acetic acid;

[3,5-Dichloro-4-(3'-heptyl-6-hydroxy-biphenyl-3-yloxy)-phenyl]-acetic acid;

[3,5-Dichloro-4-(6-hydroxy-3'-isopropyl-biphenyl-3-yloxy)-phenyl]-acetic acid;

[3,5-Dichloro-4-(6-hydroxy-3'-methoxy-biphenyl-3-yloxy)-phenyl]-acetic acid;

[3,5-Dichloro-4-(3'-ethoxy-6-hydroxy-biphenyl-3-yloxy)-phenyl]-acetic acid;

[3,5-Dichloro-4-(3'-difluoromethoxy-6-hydroxy-biphenyl-3-yloxy)-phenyl]-acetic acid;

[3,5-Dichloro-4-(6-hydroxy-3'-trifluoromethoxy-biphenyl-3-yloxy)-phenyl]-acetic acid;

[3,5-Dibromo-4-(6-hydroxy-biphenyl-3-yloxy)-phenyl]-acetic acid;

[3,5-Dichloro-4-(4-hydroxy-3-naphthalen-1-yl-phenoxy)-phenyl]-acetic acid;

{3,5-Dichloro-4-[3-(9H-fluoren-2-yl)-4-hydroxy-phenoxy]-phenyl}-acetic acid;

3-[3,5-Dibromo-4-(6-hydroxy-biphenyl-3-yloxy)-phenyl]-propionic acid;

3,5-Dibromo-4-(6-hydroxy-biphenyl-3-yloxy)-benzoic acid;

3,5-Dichloro-4-(6-hydroxy-biphenyl-3-yloxy)-benzoic acid;

[3,5-Dichloro-4-(3-cyclohexyl-4-hydroxy-phenoxy)-phenyl]-acetic acid;

{2-[3,5-Dichloro-4-(6-hydroxy-3'-methyl-biphenyl-3-yloxy)-phenyl]-acetylamino}-acetic acid;

(S)-2-{2-[3,5-Dichloro-4-(6-hydroxy-3'-methyl-biphenyl-3-yloxy)-phenyl]-acetylamino}-3-methyl-butyric acid;

(R)-2-{2-[3,5-Dichloro-4-(6-hydroxy-3'-methyl-biphenyl-3-yloxy)-phenyl]-acetylamino}-3-methyl-butyric acid;

[3,5-Dichloro-4-(6-hydroxy-biphenyl-3-yloxy)-benzoylamino]-acetic acid;

[3,5-Dichloro-4-(6-hydroxy-3'-methoxy-biphenyl-3-yloxy)-benzoylamino]-acetic acid;

[3,5-Dichloro-4-(6-hydroxy-biphenyl-3-yloxy)-benzyl]-phosphonic acid monoethyl ester; and

[3,5-Dichloro-4-(6-hydroxy-biphenyl-3-yloxy)-benzyl]-methyl-phosphinic acid.

\* \* \* \* \*

UNITED STATES PATENT AND TRADEMARK OFFICE
CERTIFICATE OF CORRECTION

| | |
|---|---|
| PATENT NO. | : 7,557,143 B2 |
| APPLICATION NO. | : 10/826100 |
| DATED | : July 7, 2009 |
| INVENTOR(S) | : Denis E. Ryono et al. |

It is certified that error appears in the above-identified patent and that said Letters Patent is hereby corrected as shown below:

On the Title Page:

Item (57) ABSTRACT:

Column 2, line 28 (excluding structures), change "–(CH2)$_m$-" to -- –(CH2)$_m$– --.

Column 2, line 35 (excluding structures), after "(–SO–)", insert -- , --.

Column 2, line 36 (excluding structures), change "(–CH2-)" to -- (–CH$_2$–) --.

In the Claims:

Claim 1:

Column 85, line 12, change "One" to -- one --.

Column 85, line 17, change "One" to -- one --.

Claim 4:

Column 85, line 37, change "supressants" to -- suppressants --.

Claim 9:

Column 87, line 39, change "benzylcarbamoyl" to -- benzylcarbamoyl) --.

Column 88, line 35, change "{35" to -- {3,5 --.

Column 88, line 59, after "acetic acid", insert -- ; --.

Signed and Sealed this
Eighteenth Day of January, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,557,143 B2 | Page 1 of 1 |
| APPLICATION NO. | : 10/826100 | |
| DATED | : July 7, 2009 | |
| INVENTOR(S) | : Ryono et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 965 days.

Signed and Sealed this
Eighteenth Day of October, 2011

David J. Kappos
*Director of the United States Patent and Trademark Office*